United States Patent [19]

Kauder et al.

[11] 4,080,364

[45] Mar. 21, 1978

[54] STABILIZATION OF POLYOLEFINS AGAINST DEGRADATIVE DETERIORATION AS A RESULT OF EXPOSURE TO LIGHT AND AIR AT ELEVATED TEMPERATURES

[75] Inventors: Otto S. Kauder, New York; Lawrence R. Brecker, Brooklyn, both of N.Y.

[73] Assignee: Argus Chemical Corporation, Brooklyn, N.Y.

[21] Appl. No.: 727,083

[22] Filed: Sep. 27, 1976

[51] Int. Cl.$^2$ ................................................ C08K 5/36
[52] U.S. Cl. ............................ 260/45.85 H; 252/406; 260/45.8 NT; 560/15; 560/147
[58] Field of Search ................ 260/45.85 H, 45.8 NT, 260/470, 481 R; 252/406

[56]  References Cited

U.S. PATENT DOCUMENTS

| 3,144,422 | 8/1964 | Homberg | 260/45.85 H |
| 3,305,580 | 2/1967 | Homberg et al. | 260/45.85 H |
| 3,629,194 | 12/1971 | Onishi et al. | 260/45.85 H |
| 3,758,549 | 9/1973 | Dexter et al. | 260/45.85 H |

*Primary Examiner*—V.P. Hoke

[57] ABSTRACT

Stabilizer mixtures that are capable of enhancing the resistance of polyolefins to degradation as a result of exposure to light and air, particularly at elevated temperatures, are obtained by reacting an α-olefin with an ester of a mercaptocarboxylic acid and a polyhydric alcohol, forming a reaction product of unknown structure containing thioether groups and carboxylic acid ester groups.

33 Claims, No Drawings

STABILIZATION OF POLYOLEFINS AGAINST DEGRADATIVE DETERIORATION AS A RESULT OF EXPOSURE TO LIGHT AND AIR AT ELEVATED TEMPERATURES

Polyolefins such as polyethylene, polypropylene and polyisobutylene have a high tendency towards degradative deterioration in physical properties as a result of exposure to light and air, particularly at elevated temperatures and over long periods of time. The polymers undergoing degradation tend to discolor, to become distorted, and to become brittle, especially when heated at elevated temperatures, and especially when exposed to air or oxygen. This deterioration is particularly marked during heat processing of the polymer in the presence of air, and during outdoor weathering in hot climates.

To meet commercial requirements, it is of course quite important that the polymer retain its physical properties during processing and thereafter. In order to enhance resistance of the polymer to such degradative deterioration in physical properties, it has been the practice to combine with the polymer multicomponent stabilizer systems in which the components complement each other in the stabilization. Various types of such stabilizer systems have been proposed, with varying degrees of commercial acceptance.

U.S. Pat. No. 3,244,650 patented Apr. 5, 1966 to Arthur C. Hecker, Otto S. Kauder and Norman L. Perry provides a system composed of three stabilizers: an organic polyhydric phenol, an organic phosphite and a polyvalent metal salt of an organic acid. To this system, U.S. Pat. No. 3,255,136 patented June 7, 1966 added a fourth ingredient, a thiodipropionic acid ester having the formula:

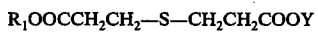

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

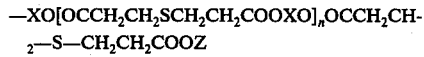

where Z is hydrogen, $R_2$ or M, n is the number of thiodipropionic acid ester units in the chain, and X is a bivalent hydrocarbon group of the type of $R_1$, that is alkylene, alkenylene, cycloalkylene, mixed alkylene-arylene and mixed alkylene-cycloalkylene radicals; hydroxyalkylene and hydroxyalkyloxyalkylene radicals; and esters thereof with aliphatic carboxylic acids; the value of n can range upwards from O, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

The thiodipropionic acid esters have been components in a variety of stabilizer systems, and are widely recognized as effective stabilizers in multicomponent systems for many purposes.

U.S. Pat. No. 3,255,151 patented June 7, 1966, proposes a stabilizer system containing an organic polysulfide and at least one additional stabilizer selected from the group consisting of phenols and organic phosphites or phosphenes. These combinations are said to give a synergistic stabilizing effectiveness, which is particularly surprising inasmuch as the organic polysulfide by itself has no noticeable stabilizing effect. The phenol alone gives an improved resistance to embrittlement with ageing, but is of little assistance in maintenance of color. The phosphite alone is a poor stabilizer, but assists in resisting discoloration. The combination of three components imparts an improved resistance to discoloration, as well as an extended stability against embrittlement.

British Pat. No. 890,468 to du Pont proposes combinations of β-thioethers of propionic acid, or of an ester of propionic acid, and a thermostabilizer, i.e., a stabilizer that has the property of stabilizing polyolefins against heat degradation, and includes phenols of various types, including polycyclic polyhydric phenols. The β-thioethers of propionic acid have the formula:

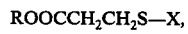

in which R is hydrogen or an alkyl or a cycloalkyl radical such as n- and isobutyl, amyl, heptyl, nonyl, decyl, lauryl, glycyl, cinnamyl, capryl, benzyl, allyl, cetyl, stearyl, palmityl, cyclohexyl, and similar groups, and X is:

1. a hydrocarbon group such as, e.g., the alkyl groups: methyl, ethyl, propyl, butyl, lauryl; the aryl groups: phenyl, naphthyl, benzyl; and such groups as p-methoxy phenyl, p-hydroxy phenyl and cyclohexyl.
2. an oxygenated-hydrocarbon group such as, e.g., the alcohol groups: hydroxymethylene, hydroxyethylene, and hydroxybutylene; the ether groups-methoxymethylene, methoxyethylene and ethoxyethylene; and acid groups and the R esters thereof- carboxymethylene, carboxyethylene, carboxypropylene and carboxybutylene; and aldehyde radicals.
3. a sulfur-hydrocarbon group such as, e.g., mercaptoethyl, mercaptopropyl, mercaptobutyl, mercaptoisobutyl, mercaptohexyl and ethiaethyl.
4. a sulfur- and oxygenated-hydrocarbon group such as, e.g., carboxyethiaethyl ($CH_2CH_2SCH_2CH_2COOH$), carboxyethiaethyldithiaethyl ($CH_2CH_2SSCH_2CH_2SCH_2CH_2COOH$), carboxyethiaisobutyl ($CH_2CH_2CH)CH_3)SCH_2CH_2COOH$) and carboxyethiapropyl ($CH_2CH_2CH_2SCH_2CH_2COOH$).
5. a sulfur- and nitrogen-containing hydrocarbon group such as, e.g., 3-benzothiazyl mercaptopropionic acid, which compounds are more specifically described in U.S. Pat. No. 2,397,960.

U.S. Pat. No. 3,378,516, patented Apr. 16, 1968 to Tholstrup, Bell and Kibler, proposes combinations including linear thiodialkanoate polyesters obtained from a thiodialkanoic acid and a diol having a molecular weight of from about 500 to about 4000, together with a phenolic antioxidant and/or a phosphite. These combinations are said to display synergistic stabilizing effectiveness.

U.S. Pat. No. 3,629,194, patented Dec. 21, 1971 to Onishi and Fukuoka, proposes esters of alkyl thiopropionic or alkyl thiobutyric acid with a polyol having up to five hydroxyl groups, in combination (optionally) with a phenolic antioxidant. The alkyl thiopropionic or alkyl thiobutyric acid esters are defined as having one of the formulae:

(1) $R-SC_nH_{2n}COOR'OOCC_nH_{2n}SR$ (2) $RSC_nH_{2n}COOC_mH_{2m}SC_mH_{2m}OOCC_nH_{2n}SR$ (3) $R''C(CH_2OX)_3$

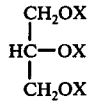
(4)

and (5) $C(CH_2OX)_4$ wherein
R is an alkyl of eight to thirty carbon atoms,
m and n are each integers of 2 or 3,
R' is an alkylene containing two to twelve carbon atoms,
R" is an alkyl containing one to twenty carbon atoms,
X is hydrogen or $-OC-C_nH_{2n}SR$, at least one of which is $-OCC_nH_{2n}SR$,
the $R_1$, R" and R" moieties in one compound being the same or different.

U.S. Pat. No. 3,758,549 patented Sept. 11, 1973 to Dexter and Steinberg proposes rather similar alkyl esters derived from alkyl thioalkanoic acids and alkane polyols, such as pentaerythritol tetrakis, 3-n-dodecylthiodipropionate, and ethylene-bis-3-n-didecylthiopropionate. These are used in combination with phenolic antioxidants to effectively stabilize polyolefins from the deleterious effects of heat and oxygen. The alkyl esters are defined by the formula:

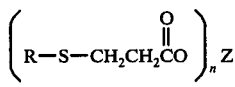

wherein
R is an alkyl group of from one to eighteen carbon atoms,
n has a value of from 2 to 4; and
Z is an aliphatic hydrocarbon of the formula:

in which y has a value of from 2 to 18 when n is 2 and a value of from 3 to 6 when n is greater than 2, the value of y in all cases being equal to or greater than that of n.

In accordance with the instant invention, stabilizer mixtures for poly-α-olefins are provided by reacting an α-olefin with a multifunctional ester of a mercaptocarboxylic acid and a polyhydric alcohol. The term "multifunctional" as used herein refers to the functional groups mercapto SH and ester COOR of the ester of the mercaptocarboxylic acid and polyhydric alcohol. There is at least one of each, and there can be as many as eight of each. In the course of the reaction, one or more mercapto groups of the ester are extinguished, and a reaction product is formed that contains thioether groups and carboxylic acid ester groups, with the residue of the ester of the mercaptocarboxylic acid and polyhydric alcohol being attached to the α-olefin in some manner which is at present undetermined.

The reaction mixture is a complex assortment of reaction products, in varying amounts. The mixture is more effective, however, than the alkyl esters derived from alkyl thioalkanoic acids and alkane polyols which are described in the Dexter and Steinberg Pat. No. 3,758,549 and the Onishi et al Pat. No. 3,629,194, which are prepared by direct esterification reactions starting from the alkyl thioalkanoic acid and the polyol. It is apparent that unknown byproducts of this reaction that are present in the reaction mixture in some way cooperate with any alkyl thioalkanoic acid polyol ester that may be present (the presence of which has not yet been confirmed), so that a synergistic interaction of the reaction mixture components is postulated. Inasmuch as the reaction product is of unknown composition, it is defined in terms of the starting material from which it is obtained.

This stabilizer mixture can be used with any poly-α-olefin compositions having an enhanced resistance to degradative deterioration due to the action of light and/or heat, and comprising such a reaction mixture as a primary stabilizer component. Such stabilizer mixtures can be used in combination with antioxidants, such as phenols and organic phosphites, as well as other conventional poly-α-olefin heat and light stabilizers.

The invention further provides a process for preparing such stabilizer mixtures by reacting an α-olefin with a multifunctional ester of a mercaptocarboxylic acid and a polyhydric alcohol, at a temperature at which the reaction proceeds up to 200° C; recovering the resulting reaction mixture; and employing it substantially intact as a stabilizer for poly-α-olefins.

The stabilizer mixtures in accordance with the invention are prepared by reacting an α-olefin or a compound containing an α-olefin with a multifunctional ester of a mercaptocarboxylic acid and a polyhydric alcohol in a molar ratio ester: α-olefin within the range from 1:1 to 1:8. The α-olefin adds to the ester in some manner which is at present undetermined, and forms a reaction product containing thioether groups and carboxylic acid ester groups. A variety of reaction products can be postulated; the reaction mixture is apparently a complex assortment of unreacted starting materials and the various possible reaction products, in varying amounts.

It has been found that the reaction mixture is an effective stabilizer, more effective than components isolated therefrom, including unreacted starting materials, so that it appears that the reaction mixture is a synergistic mixture of unknown constituents, of complex and presently unknown compositions and structure. Accordingly, this reaction mixture can be defined only in terms of the starting materials from which it is obtained.

As the compound containing an α-olefinic group, any α-olefin can be employed having the general formula

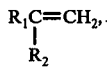

where $R_1$ and $R_2$ are selected from the group consisting of hydrogen and monovalent organic groups having from one to about thirty carbon atoms, including hydrocarbon groups, of both open chain and cyclic structure, including aliphatic, cycloaliphatic, aromatic and terpene hydrocarbons containing only carbon and hydrogen. The $R_1$ and $R_2$ groups can also include radicals with additional inert substituents, including oxyether, thioether and hydroxyl groups, as well as polysulfide groups.

Exemplary α-olefins include ethylene, propylene, butylene, isobutylene, pentylene, hexylene, heptylene, octylene, 2-ethyl-1-hexene, nonylene, decylene, undecylene, dodecylene, tridecylene, tetradecylene, heptadecylene, octadecylene, behenylene, eicosylene; α-cyclopropylethylene, α-cyclobutylethylene, α-cyclopentylethylene, α-cyclohexylethylene, α-cycloheptylethylene, α-cyclooctylethylene; styrene; and alkyl substituted and alkenyl substituted such groups including, α-(methylcyclohexyl) ethylene, α-(ethylcyclohexyl) ethylene, α-(propylcyclopentyl) ethylene, α-(dimethylcyclohexyl) ethylene, α-(trimethylcyclohexyl) ethylene, α-(ethylcyclooctyl) ethylene; α-methylstyrene, α-ethyl styrene, camphene, β-pinene.

The mercaptocarboxylic acid is esterified with a polyhydric alcohol, forming a multifunctional mercaptocarboxylic acid ester of the structure:

wherein:
m is the number of HS groups, and is a number from one to about four;
n is the number of mercapto groups and is a number from three to about eight;
R is an organic group derived from a polyhydric alcohol of the formula $R'(OH)_p$ where p is a number from three to about eight, but preferably from three to six;
Z is a bivalent alkylene radical carrying at least one HS group in a position alpha or beta to a COOR group, and can contain additional free carboxylic acid or carboxylic ester groups, and mercapto groups. The Z radical has from one to about five carbon atoms.

The $[[HS]_m—Z—COO]_n—R—[OH]_{p-n}$ esters are derived from
mono- or poly α and β-mercapto monocarboxylic acids by removal of the hydrogen atom of the carboxylic acid group COOH in reaction with one or more hydroxyl groups OH of the polyol. These include the esters of aliphatic acids which contain from one to four mercapto groups, such as, for example, esters of mercaptoacetic acid, α- and β- mercaptopropionic acid, α- and β-mercaptobutyric acid, α- and β-mercaptovaleric acid and α- and β-mercaptohexanoic acid.

R is the nucleus of the polyhydric alcohol $R'(OH)_p$ (in which p is a number from three to eight) to which the hydroxyl groups are attached, and can include unesterified alcohol hydroxyl groups, as well as other inert substituents, such as oxyether, thioether and polysulfide groups, and heterocyclic rings formed from such hydroxyl groups and including nitrogen in the ring structure, such as, for example, an isocyanurate ring.

Thus, R can be alkylene, alkenylene, arylene, mixed alkylene, arylene, mixed aryl-alkylene, cycloaliphatic and heterocyclic, and can contain from about two to about twelve carbon atoms, and can also contain ester groups, oxyether, thioether and polysulfide groups, hydroxyl groups, halogen atoms and other inert substituents.

Exemplary polyhydric alcohols include pentaerythritol, sorbitol, mannitol, trimethylolpropane, trimethylolethane, trimethylolbutane, di-trimethylolpropane, dipentaerythritol, tripentaerythritol, cyclohexane-1,2,4-trimethanol, and hexahydroxycyclohexane, pentahydroxycyclopentane, trihydroxycycloheptane, and benzene-1,2,4,5-tetramethanol.

The polyhydric alcohol need not be a single compound. Many of the commercially available and inexpensive mixtures are suitable and advantageous.

The reaction in accordance with the invention takes place in the presence of a free radical catalyst, i.e. a catalyst which provides a free radical upon decomposition. These catalysts are known per se, and form no part of the invention. The free radical catalyst should have a half life at 60° C within the range from 2 to 2,000 minutes.

A preferred class of free radical catalysts is the organic peroxides, which include:

Peresters, such as tertiary-butyl perbenzoate, tertiary-butyl peroctoate, tertiary-butyl perpivalate, tertiary-butyl perneodecanoate, 2,5-dimethyl-2,5:bis (2-ethylhexoyl peroxy) hexane, 2,5-dimethyl-2,5-bis (benzoyl peroxy) hexane, tertiary-butyl peroxypentanoate, tertiarybutyl peroxydecanoate, tertiary-butyl peroxy-2-methylpropionate, tertiarybutyl peroxy-2-methylpentanoate, tertiary-butyl peroxy-2-ethylbutyrate, tertiary-butyl peroxy-2-ethylhexanoate, tertiary-butyl peroxyneopentanoate, tertiary-butyl peroxyneooctanoate, 2,5-dimethylhexane-2,5-diperoxypentanoate, 2,5-dimethylhexane-2,5-diperoxyoctanoate, 2,5-dimethylhexane-2,5-diperoxydecanoate, 2,5-dimethylhexane-2,5-diperoxy-2-methylpropionate, 2,5-dimethylhexane-2,5-diperoxy-2-methylpentanoate, 2,5-dimethylhexane-2,5-diperoxy-2-ethylbutyrate, 2,5-dimethylhexane-2,5-diperoxyneopentanoate, 2,5-dimethylhexane-2,5-diperoxyneooctanoate, 2,5-dimethylhexane-2,5-diperoxyneodecanoate, 2,5-dimethylhexyne-3-2,5-diperoxypentanoate, 2,5-dimethylhexyne-3-2,5-diperoxyoctanoate, 2,5-dimethylhexyne-3-2,5-diperoxydecanoate, 2,5-dimethylhexyne-3-2,5-diperoxy-2-methylpropionate, 2,5-dimethylhexyne-3-2,5-diperoxy-2-methylpentanoate, 2,5-dimethylhexyne-3-2,5-diperoxy-2-ethylbutyrate, 2,5-dimethylhexyne-3-2,5-diperoxy-2-ethylhexanoate, 2,5-dimethylhexyne-3-2,5-diperoxyneopentanoate, 2,5-dimethylhexyne-3-2,5:diperoxyneooctanoate, 2,5-dimethylhexyne-3-2,5-diperoxyneodecanoate, 2,7-dimethyloctane-2,7-diperoxypentanoate, 2,7-dimethyloctane-2,7-diperoxyoctanoate, 2,7-dimethyloctane-2,7-diperoxydecanoate, 2,7-dimethyloctane-2,7-diperoxy-2-methylpropionate, 2,7-dimethyloctane-2,7-diperoxy-2-methylpentanoate, 2,7-dimethyloctane-2,7-diperoxy-2-ethylbutyrate, 2,7-dimethyloctane-2,7-diperoxy-2-ethylhexanoate, 2,7-dimethyloctane-2,7-diperoxyneopentanoate, 2,7-dimethyloctane-2,7-diperoxyneooctanoate, 2,7-dimethyloctane-2,7-diperoxyneodecanoate, 2,4,7,9-tetramethyldecyne-3,4,7-diperoxy2-ethylhexanoate, tertiary-butyl peroxyacetate, tertiary-butyl peroxymaleic acid, tertiary-butyl peroxyisobutyrate, tertiary-butyl peroxytoluate, tertiarybutyl peroxycrotonate, di-tertiary-butyl diperoxyphthalate;

Perketals such as ethyl-3,3-bis (tertiary-butyl peroxy) butyrate, 1,1-bis (tertiary-butyl peroxy) yclohexane, 2,2-bis (tertiary-butylperoxy) butane, 1,1-bis (tertiary-butyl peroxy) 3,3,5-trimethylcyclohexane;

Diacyl peoxides, such as lauroyl peroxide, acetyl-2-ethyl hexanoyl peroxide, decanoyl peroxide, acetyl peroxide, benzoyl peroxide, 2,4-dichlorobenzoyl peroxide, p-chlorobenzoyl peroxide, isobutyryl peroxide, diisoanoyl peroxide, pelargonyl peroxide, propionyl peroxide, and di-toloyl peroxide;

Ketone peroxides, such as methyl ethyl ketone peroxide, acetyl acetone peroxide, cyclohexanone peroxide and bis(1-hydroxycyclohexyl) peroxide;

Dibasic acid peroxides, such as succinic acid peroxide;

Sulfonyl acyl peroxides, such as acetyl cyclohexyl sulfonyl peroxide and acetyl sec-heptylsulfonyl peroxide;

Peroxy carbonates, such as tertiary-butylperoxy isopropyl carbonates, such as tertiary-butylperoxy isopropyl carbonate;

Peroxy dicarbonates, such as bis (4-tertiary-butylcyclohexyl) peroxydicarbonate, dibenzyl peroxydicarbonate, dicyclohexyl peroxydicarbonate, diisopropyl peroxydicarbonate, di (n-propyl) peroxydicarbonate, di (sec-butyl) peroxydicarbonate, di (2-ethylhexyl) peroxydicarbonate;

Hydroperoxides such as tertiary-butyl hydroperoxide, 1,1,3,3-tetramethyl butyl hydroperoxide, cumene hydroperoxide, 2,5-dimethylhexane2,5-dihydroperoxide, diisopropylbenzene hydroperoxide, and p-menthane hydroperoxide;

Dialkyl peroxides, such as di-tertiary-butyl peroxide, bis (tertiary-butyl peroxyisopropyl) benzene, a,a:bis (tertiary-butyl peroxydiisopropylbenzene, n-butyl-4,4-bis (tertiary-butylperoxy) valerate, dicumyl peroxide, 2,5-dimethyl-2,5-bis (tertiary-butyl peroxy) hexane and 2,5-dimethyl-2,5-bis (tertiary-butyl peroxy) hexyne 3.

Other free radical catalysts which can be used include oxygen, ozone, chlorine, persulfates, inorganic peroxides, and azo compounds such as azobisisovaleronitrile. Certain of these compounds may be made more effective and efficient if used in conjunction with accelerators. Examples of accelerated systems may include benzoyl peroxide with dimethylaniline as an accelerator. Included in this class are reagents or components which are generated in situ in the composition.

The free radical catalyst is usually added in an amount ranging from about 0.0005 to about 25% by weight of the composition, with the preferred range being from about 0.5 to about 5% by weight.

The reaction proceeds at room temperature, and even at temperatures slightly below room temperature, down to about 10° C. However, a more rapid reaction is obtained at elevated temperatures. In general, a reaction temperature within the range from about 50° to about 120° C is preferred. At temperatures about 120° C, the free radical catalyst may be too unstable, and may be decomposed faster than it can catalyze the reaction. Thus although higher reaction temperatures can be used, in general the reaction temperature will not exceed about 200° C.

The stabilizer mixtures of the invention can be used without addition of other stabilizers in enhancing the resistance to deterioration of poly-α-olefins to light and air. However, for best overall effect these stabilizer mixtures are best used in a stabilizer system in combinations with one or more poly-α-olefin heat and light stabilizers.

The stabilizer system of the invention comprises one or more stabilizer mixtures of the invention in combination with at least one poly-α-olefin stabilizer, and preferably, two or more such stabilizers. It is well known that in the case of α-olefin polymers, combinations of stabilizers can be complementary, and can enhance the resistance of the olefin polymer to oxidative deterioration. Such enhanced stabilizing effectiveness when present in the α-olefin polymer stabilizer combination continues to be evidenced in the presence of the stabilizer system of the invention.

Stabilizer systems of the invention comprising a stabilizer mixture of the invention and an α-olefin polymer stabilizer can be formulated and marketed as such, ready for use by the converter of the α-olefin polymer into useful products.

A variety of α-olefin polymer stabilizers can be employed of which the following are exemplary.

The organic phosphite can be any organic phosphite having one or more organic radicals attached to phosphorus through oxygen. These radicals can be monovalent radicals in the case of the triphosphites, diphosphites and monophosphites, which can be defined by the formula:

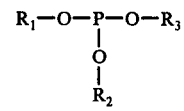

in which $R_1$, $R_2$ and $R_3$ are selected from the group consisting of hydrogen, alkyl, alkenyl, aryl, alkaryl, aralkyl, and cycloalkyl groups having from one to about thirty carbon atoms.

Also included are the organic phosphites having a bivalent organic radical forming a heterocyclic ring with the phosphorus of the type:

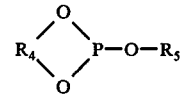

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$.

Also useful in the compositions of the invention are mixed heterocyclic-open chain phosphites of the type:

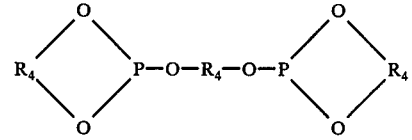

More complex phosphites are formed from trivalent organic radicals, of the type:

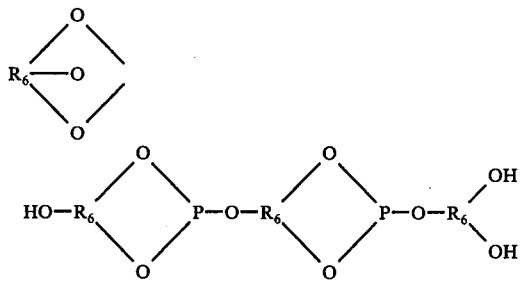

in which $R_6$ is a trivalent organic radical of any of the types of $R_1$ to $R_5$, inclusive, as defined above.

A particularly useful class of complex phosphite are the tetraoxadiphosphaspiro undecanes of the formula

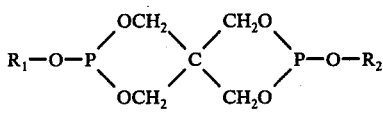

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl.

An expecially preferred class of organic phosphites have a bicyclic aromatic group attached to phosphorus through oxygen, with no or one or more phenolic hydroxyl groups on either or both of the aromatic rings. These phosphites are characterized by the formula:

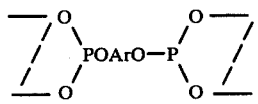

or

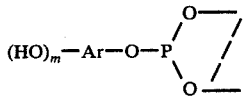

in which Ar is a mono or bicyclic aromatic nucleus and m is an integer of from 0 to about 5. is one or a plurality of organic radicals as defined above for $R_1$ to $R_6$, taken singly or together in sufficient number to satisfy the valences of the two phosphite oxygen atoms. can also be hydrogen, and can include additional bycyclic aromatic groups of the type $(HO)_m$-Ar.

The term "organic phosphite" as used herein is inclusive of the above-described mono-, di- and triphosphites. Usually, the phosphite will not have more than about sixty carbon atoms.

Exemplary are monophenyl di -2-ethylhexyl phosphite, diphenyl mono-2-ethylhexyl phosphite, di-isooctyl monotolyl phosphite, tri-2-ethylhexyl phosphite, phenyl dicylohexyl phosphite, phenyl diethyl phosphite, triphenyl phosphite, tricresyl phosphite, tri(dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri(2-cyclohexylphenyl) phosphite, tri-α-naphthyl phosphite, tri(phenylphenyl) phosphite, tri(2-phenyl ethyl) phosphite, monododecyl phosphite, di(p-tert-butyl phenyl) phosphite, decyl phenyl phosphite, tert-butyl-phenyl 2-ethylhexyl phosphite, ethylene phenyl phosphite, ethylene t-butyl phosphite, ethylene isohexyl phosphite, ethylene isooctyl phosphite, ethylene cyclohexyl phosphite, 2-phenoxy1,3,2-dioxaphosphorinane, 2-butoxy-1,3,2-dioxyphosphorinane, 2-octoxy5,5-dimethyl-dioxaphosphorinane, 2-cyclohexyloxy-5,5-diethyl dioxaphosphorinane, monophenyl phosphite, 2-ethylhexyl phosphite, isooctyl phosphite, cresyl phosphite, t-octylphenyl phosphite, t-butyl phosphite, diphenyl phosphite, diisooctyl phosphite, dicresyl phosphite, dioctylphenyl phosphite, didodecyl phosphite, di-α-naphthyl phosphite, ethylene phosphite, butyl cresyl phosphite, phenyl-mono-2-ethylhexyl phosphite, isooctyl monotolyl phosphite and phenyl cyclohexyl phosphite.

Exemplary pentaerythrityl phosphites are 3,9-diphenoxy-2,4,8,10-tetraoxa-3,9-diphosphaspiro-(5,5)-undecane (diphenyl-pentaerythritol-diphosphite), 3,9-di(decycloxy)-2,4,8,10-tetraoxa-3,9-diphosphaspiro (5,5) undecane, 3,9-di(isodecyloxy) 2,4,8, 10-tetraoxa-3,9-diphosphaspiro-(5,5)-undecane, 3,9-di(octadecyloxy)2,4,8,10-tetraoxa-3,9-diphosphaspiro-(5,5)-undecane, 3phenoxy-9-isodecyloxy-2,4,8,10-tetraoxa-3,9-diphosphaspiro-(5,5)-undecane, 3,9-di(methoxy)2,4,8,10-tetraoxa-3,9-diphosphaspiro(5,5)-undecane 3,9-di(-lauryloxy)-2,4,8,10-tetraoxa-3,9-diphosphaspiro(5,5)-undecane,3,9-di-p-tolyloxy -2,4,8,10 tetraoxa-3,9-diphosphaspiro-(5,5)-undecane; 3,9-di(methoxyethyloxy)2,4,8,10-tetraoxa-3,9,diphosphaspiro-(5,5)-undecane; 3-methoxyethyloxy-9-isodecyloxy-2,4,8,10-tetraoxa-3,9-diphosphaspiro-(5,5)-undecane; 3,9-di(ethoxyethyloxy)2,4,8,10-tetraoxa-3,9-diphosphaspiro-(5,5)-undecane; 3,9-di(butoxyethyloxy) -2,4,8,10-tetraoxa-3,9-diphosphaspiro-(5,5)-undecane; 3-methoxyethyloxy-9-butoxyethyloxy-2,4,8,10-tetraoxa-3,9-diphosphaspiro (5,5)-undecane; 3,9-di(methoxyethoxyethyloxy)2,4,8,10-tetraoxa-3,9-diphosphaspiro-(5,5)-undecane; 3,9-di(butoxyethoxyethyloxy) -2,4,8,10-tetraoxa-3,9-diphosphaspiro-(5,5)-undecane; 3,9-di(methoxyethyoxethyloxy)-2,4,8,10-tetraoxa-3,9-diphosphaspiro-(5,5)-undecane; 3,9-di(methoxy (polyethoxy)ethyloxy)-2,4,8,10-tetraoxa-3,9-diphosphaspiro (5,5) undecane (where the (polyethoxy)ethyloxy group has an average molecular weight of 350) 3,9-di(methoxy (polyethoxy)ethyloxy)-2,4,8,10-tetraoxa-3,9-diphosphaspiro (5,5) undecane (where the (polyethoxy)ethyloxy group has an average molecular weight of 550).

Exemplary of the bis aryl phosphites are: bis(4,4'-thio-bis(2-tertiary butyl-5-methyl-phenol)) isooctyl phosphite, mono(4,4'-thio-bis(2-tertiary-butyl-5-methylphenol)) di-phenyl phosphite, tri-(4,4'-n-butylidene-bis(2-tertiary-butyl-5-methyl-phenol)) phosphite, (4,4'-benzylidene-bis(2-tertiary-butyl-5-methyl-phenol)) di-phenyl phosphite, isooctyl 2,2'-bis(-parahydroxyphenyl) propane phosphite, tri-decyl 4,4'-n-butylidene-bis(-2-tertiary butyl-5-methylphenol)phosphite, 4,4'-thiobis(2-tertiary butyl-5-methylphenol) phosphite, 2-ethylhexyl-2,2'-methylene-bis(4-methyl-6-1'-methylcyclohexyl) phenol phosphite, tri(-2,2'-bis-(para-hydroxyphenyl) propane) phosphite, tri(-4,4'-thio-bis(2-tertiary-butyl-5-methyl-phenol) phosphite, isooctyl-(2,6-bis(2'-hydroxy-3,5-dinonylbenzyl)-4-nonyl phenyl)) phosphite, tetra-tridecyl 4,4'n-butylidene-bis(2-tertiary butyl-5-methyl phenyl)diphosphite, tetra-isooctyl 4,4'-thiobis(2-tertiary butyl5-methyl phenyl) diphosphite, 2,2'-methylene-bis(4-methyl 6-1'-methyl cyclo-hexyl phenyl) polyphosphite, isooctyl-4,4'-isopropylidene-bis-phenyl-polyphosphite, 2-ethylhexyl-2,2'-methylene-bis(4-methyl-6,1'-methyl-cyclohexyl) phenyl triphosphite, tetra-tridecyl4,4'-oxydiphenyl diphosphite, tetra-n-dodecyl-4,4'-n-butylidenebis (2-tertiary-butyl-5-methylphenyl) diphosphite, tetra-tridecyl-4,4'-iso-propylidene bisphenyl diphosphite, hexa-tridecyl butane-1,1,3-tris(2'-methyl-5'-tertiary-butylphenyl-4'-)triphosphite.

The phenol stabilizers contain one or more phenolic hydroxyl groups, and one or more phenolic nuclei and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compond then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one or four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure;

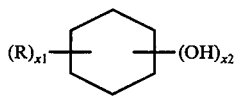

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol employed in the stabilizer combination is one having at least two aromatic nuclei linked by a polyvalent linking radical, as defined by the formula:

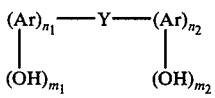

wherein Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings: each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g. chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

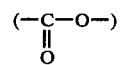

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluorenyl groups.

When Ar is a benzene nucleus, the polyhydric polycyclic phenol has the structure:

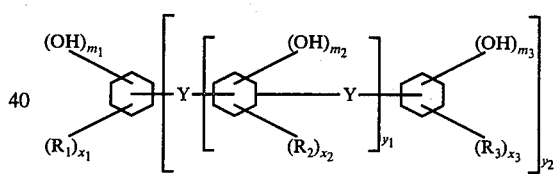

wherein $R_1$, $R_2$ and $R_3$ are inert substituent groups as described in the previous paragraph, $m_1$ and $m_3$ are integers from one to a maximum of five, $m_2$ is an integer from one to a maximum of four, $x_1$ and $x_3$ are integers from zero to four, and $x_2$ is an integer from zero to three; $y_1$ is an integer from zero to about six and $y_2$ is an integer from one to five, preferably one or two.

Preferably, the hydroxyl groups are located ortho and/ or para to Y.

Exemplary Y groups are alkylene, alkylidene, and alkenylene arylene, alkyl arylene, arylalkylene, cycloalkylene, cycloalkylidene, and oxa- and thia-substituted such groups; carbonyl groups, tetrahydrofuranes, esters and triazino groups. The Y groups are usually bi, tri, or tetravalent, connecting two, three or four Ar groups. However, higher valence Y groups, connecting more than four Ar groups, can also be used. According to their constitution, the Y groups can be assigned to subgenera as follows:

(1) Y groups where at least one carbon in a chain or cyclic arrangement connect the aromatic groups, such as

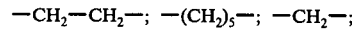

-continued

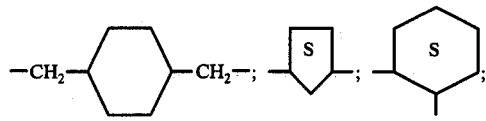
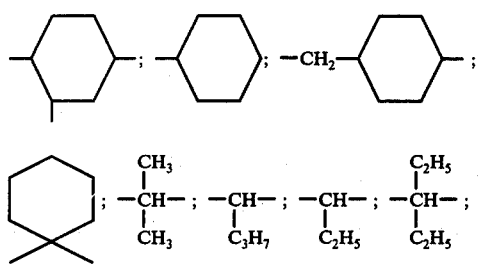
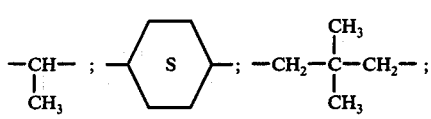
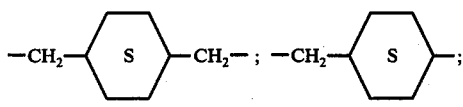
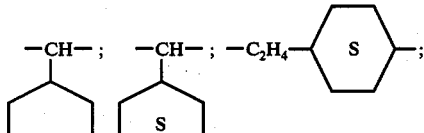
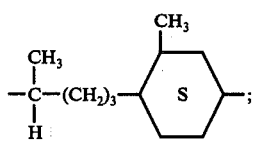
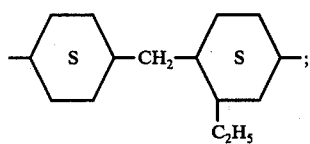
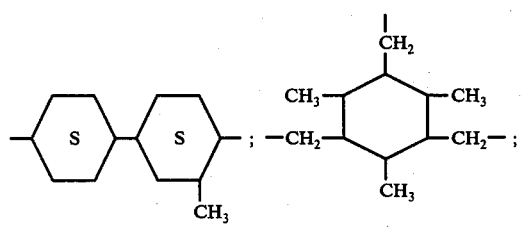
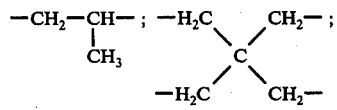
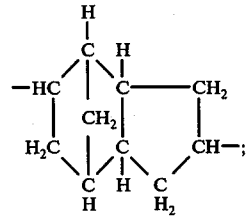

-continued

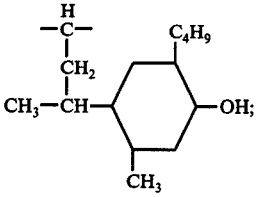

(2) Y groups where only atoms other than carbon link the aromatic rings, such as

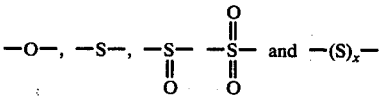

where x is a number from one to ten;

(3) Y groups made up of more than a single atom including both carbon and other atoms linking the aromatic nuclei, such as

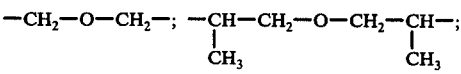
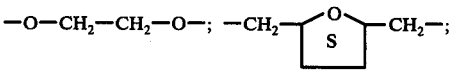
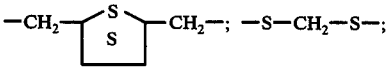
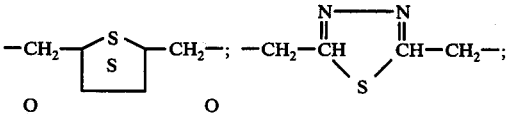
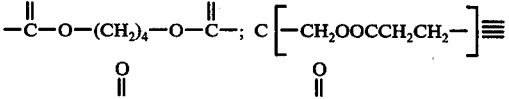
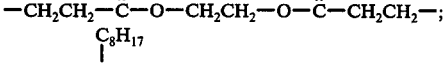
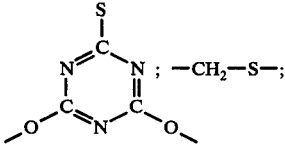

$-CH_2-S-CH_2-$; and 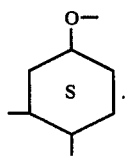

Although the relation of effectiveness to chemical structure is insufficiently understood, many of the most effective phenols have Y groups of subgenus 1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-ditert-butyl-4-methyl phenol, 2-tert-butyl-4-methoxy phenol, 2,4-dinonyl phenol, 2,3,4,5,-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o- and m-tertbutyl-p-hydroxy-anisole,p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol methyl-p-hydroxybenzoate, p-di-chlorobenzoylaminophenol and p-hydroxysalicyl anilide.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-ditertiary-butyl-resorcinol, 2,6diisopropyl-phloroglucinol.

Exemplary polyhydric polycyclic phenols are methylenebis-(2,6-ditertiarybutyl-phenol), 2,2-bis-(4-hydroxy phenyl)-propane, methylene-bis(p-cresol), 4,4'-benzylidenebis-(2-tertiary butyl-5-methylphenol), 4,4'-cyclohexylidenebis-(2-tertiary butylphenol), 2,2'-methylenebis(4-methyl-6-(1'-methyl-cyclohexyl)-phenol), 2,6-bis(2'-hydroxy-3'-tertiary-butyl-5'-methylbenzyl)-4-methylphenol, (2-tertiary-butyl-5-methylphenol), 2,2'-bis(4-hydroxy-phenyl) butane, ethylene-bis-(p-cresol), 4,4'-oxobis-phenol, 4,4'-oxobis (3-methyl-5-isopropyl-phenol), 4,4'oxobis-(3-methyl-phenol), 2,2'-oxobis-(4-dodecyl-phenol), 2,2'-oxobis(4-methyl-5-tertiary-butyl-phenol) 4,4'-thio-bis-phenol; 4,4'-thio-bis(3-methyl-6-tertiary-butyl-phenol), 2,2'-thio-bis-(4-methyl-6-tertiarybutyl-phenol), 4,4'-n-butylidene-(2-t-butyl-5-methyl-phenol), 2,2'-methylene-bis-(4-methyl-6,(1'-methyl-cyclohexyl)-phenol), 4,4'-cyclohexylenebis-(2-tertiary-butyl-phenol), 2,6-bis-(2'-hydroxy-3'-t'-butyl5'-methyl-benzyl)-4-methyl-phenol, 4,4'-oxobis (naphthalene-1,5-diol), 1,3'-bis(naphthalene-2,5-diol)propane, and 2,2'-butylenebis-(naphthalene-2,7-diol), (3-methyl-5-tert-butyl-4-hydroxyphenyl)-4'-hydroxyphenyl)propane, 2,2'-methylenebis-(4-methyl-5-isopropylphenol), 2,2'-methylenebis-(5-tert-butyl-4-chlorophenol), (3,5-di-tert-butyl4-hydroxyphenyl)-(4'-hydroxyphenyl)ethane, (2-hydroxy-phenyl)(3',5'-di-tert-butyl-4'4-hydroxy-phenyl)ethane, 2,2'-methylenebis(4-octylphenol), 4,4'-propylenebis-(2-tert-butyl-phenol), 2,2'-isobutylenebis-(4-nonylphenol), 2,4-bis-(4-hydroxy-3-t-butylphenoxy)6-(n-octylthio)-1,3,5-triazine, 2,4,6-tris(4-hydroxy-3-t-butylphenoxy)-1,3,5-triazine, 2.2'-bis-(3-t-butyl-4-hydroxyphenyl) thiazolo-(5,4-d)thiazole, 2,2'-bis-(3-methyl-5-t-butyl-4-hydroxyphenyl) thiazolo-(5,4-d)-thiazole, 4,4'-bis-(4-hydroxy-phenyl)pentanoic acid octadecyl ester, cyclopentylene-4,4'-bisphenol, 2-ethylbutylene-4,4'-bisphenol, 4,4'-cyclooctylenebis(2-cyclohexylphenol), β,β-thiodiethanolbis(3-tert-butyl-4-hydroxyphenoxy acetate), 1,4-butanediobis(3-tert-butyl-4-hydroxyphenoxy acetate), pentaerythritoltetra(4-hydroxyphenol propionate), 2,4,4'-tri-hydroxy benzophenone, bis(2-tert-butyl-3-hydroxy-5-methylphenyl) sulfide, bis(2-tert-butyl-4-hydroxy-5-methylphenyl) sulfide, bis(2-tert-butyl-4-hydroxy-5-methylphenyl sulfoxide), bis-(3-ethyl-5-tert-butyl-4-hydroxy benzyl) sulfide, bis(2-hydroxy-4-methyl-6-tert-butyl phenyl) sulfide, 4,4'-bis(4-hydroxyphenyl) pentanoic acid octadecyl thiopropionate ester, 1,1,3-tris(2'-methyl-4'-hydroxy-5'-tert-butylphenyl) butane, 1,1,3-tris-(1-methyl-3-hydroxy-4-tert-butylphenyl) butane, 1,8-bis(2-hydroxy-5-methylbenzoyln-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)bis-(4-methoxy-6-tert-butyl phenol) and pentaerythritol hydroxyphenyl propionate.

A particularly desirable class of polyhydric polycyclic phenols are the dicyclopentadiene polyphenols, which are of the type:

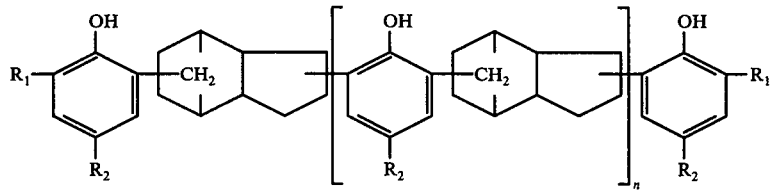

in which $R_1$ and $R_2$ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri(2-tert-butyl-4-methyl-phenol) of the formula:

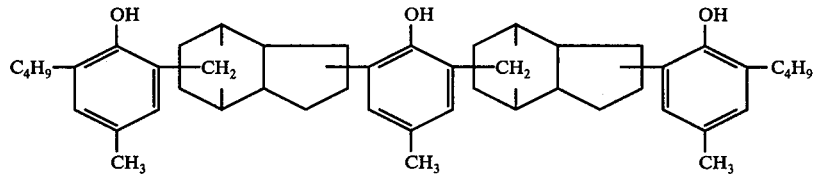

The polyhydric polycyclic phenols used in the invention can also be condensation products of phenol or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see, e.g., U.S. Pat. No. 3,124,555, U.S. Pat. No. 3,242,135, British patent No. 961,504.

The thiodipropionic acid ester has the following formula:

R₁OOCCH₂CH₂-S-CH₂CH₂COOY in which R₁ is an organic radical selected from the group consisting of hydrocarbon radicals such as alkyl, alkenyl, aryl, cycloalkyl, mixed alkyl aryl, and mixed alkyl cycloalkyl radicals; and esters thereof with aliphatic carboxylic acids; and Y is selected from the group of a) hydrogen, b) a second R radical R₂, which can be the same as or different from the R₁ radical, c) a polymeric chain of n thiodipropionic acid ester units:

R₁O[OCCH₂CH₂SCH₂CH₂COOXO]ₙOCCH₂CH₂-S-CH₂CH₂COOZ wherein Z is hydrogen, R₂ or M; n is the number of thiodipropionic acid ester units in the chain; and X is a bivalent hydrocarbon group of the type of R₁; the value of n can range upwards from 1, but there is no upper limit on n except as is governed by the ratio of carbon atoms to sulfur atoms as stated below; and d) a polyvalent metal M of Group II of the Periodic Table such as zinc, calcium, cadmium, barium, magnesium and strontium.

The molecular weights of the R and Y radicals are taken such that with the remainder of the molecule, the thiodipropionic ester has a total of from about ten to about sixty carbon atoms per sulfur atom.

Accordingly, the various thiodipropionic acid ester species coming within the above-mentioned categories within the general formula can be defined as follows:

(a) R₁OOCCH₂CH₂SCH₂CH₂COOH
(b) R₁OOCCH₂CH₂SCH₂CH₂COOR₂
(c)    R₁O[OCCH₂CH₂SCH₂CH₂COOX-O]ₙOCCH₂CH₂SCH₂CH₂COOZ
(d) [R₁OOCCH₂CH₂SCH₂CH₂COO]₂M

In the above formulae, R₁ and R₂, M, X and Z are the same as before. In the polymer c), as in the other forms of thiodipropionic acid esters, the total number of carbon atoms per sulfur atom is within the range from about ten to about sixty.

The R radical of these esters is important in furnishing compatibility with the polypropylene. The Y radical is desirably a different radical, R₂ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described below.

The aryl, alkyl, alkenyl and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl- and aryl-substituted alkylene radicals such as 1,2-propylene

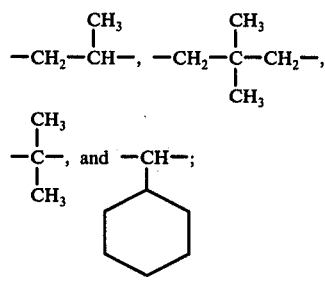

arylene radicals such as phenylene

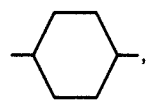

methylenephenylene

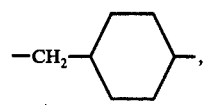

dimethylene phenylene,

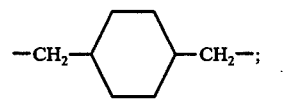

and alicyclene radicals such as cyclohexylene

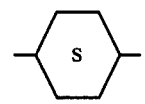

and cyclopentylene

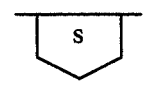

As exemplary of the thiodipropionic acid esters which can be used, there can be mentioned the following: monolauryl thiodipropionic acid, dilauryl thiodipropionate, butyl stearyl thiodipropionate, di(2-ethylhexyl)-thiodipropionate, diisodecylthiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soybean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

When the compound is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic nonnitrogenous monocarboxylic acid having from six to twenty-four carbon atoms. The aliphatic, aromatic, alicyclic and oxygencontaining heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reaction, such as by mixing the acid, or anhydride with the corresponding oxide or hydroxide of the metal in a liquid solvent, and heating, if necessary, until salt formation is complete.

The hydrocarbon sulfides and polysulfides can contain one sulfur atom or two or more sulfur atoms linked in a polysulfide unit. Usually, the sulfides and polysulfides will not have more than fifty carbon atoms. They can be defined by the formula:

$$R(S)_n\text{-}R$$

wherein $n$ is the number of sulfur atoms and ranges from one to about six, and R is an organic radical having from one to about thirty carbon atoms, such as alkyl, aryl, alkaryl, aralkyl, and cycloalkyl. The following compounds are typical: dibutyl sulfide, didecyl sulfide, diphenyl sulfide, dibenzyl sulfide, butyl octyl sulfide, di-n-dodecyl trisulfide, di-tertiary dodecyl disulfide, di-para-tertiary butyl phenyl trisulfide, dibenzyl disulfide, dibenzyl tetra sulfide, and dibenzyl trisulfide.

Light stabilizers for olefin polymers can also be added, for example, 2-hydroxy benzophenones, o-hydroxyphenylbenzotriazoles, 1-dioxides of $\alpha,\beta$-benzoisothiazolone and 1,3,5-triazines and nickel organophosphites as disclosed in application Ser. No. 487,614, now U.S. Pat. No. 3,395,112, dated July 30, 1968.

In another embodiment of the invention, as previously indicated, one or more stabilizer mixtures of the invention can be combined with the $\alpha$-olefin polymer. Such compositions are readily marketed by the polymer manufacturer as an $\alpha$-olefin polymer which can be combined with the usual $\alpha$-olefin polymer stabilizers by the converter in the usual way, without any modification whatsoever, so as to obtain the benefits of the invention due to the presence in the formulation of a stabilizer mixture of the invention. Such compositions have the special advantage that they can be processed using the usual techniques, and, in addition, the usual $\alpha$-olefin polymer stabilizer systems will behave virtually in their normal way.

The amount of total stabilizer including any $\alpha$-olefin polymer stabilizer and the stabilizer mixture of the invention is within the range from about b 0.0001 to about 7.5%, preferably from 0.01 to 5%. Of this, any $\alpha$-olefin polymer stabilizer comprises from about 0.001 to about 5% by weight. The preferred $\alpha$-olefin polymer stabilizer comprises from about 0.025 to about 1% of a phenol, and optionally, from about 0.05 to about 1.25% of a phosphite, and from about 0.025 to about 0.75% of a polyvalent metal salt, when present.

The stabilizer mixtures of the invention and any $\alpha$-olefin polymer stabilizers may be formulated as a simple mixture for incorporation in the polymer by the polymer manufacturer or by the converter. An inert organic solvent can be used to facilitate handling, if the ingredients do not form a homogeneous mixture or solution.

Polypropylene solid polymer can be defined in a manner to differentiate it from other polyolefins as having a density within the range of from 0.86 to 0.91, and a melting point above 150° C. The stabilizer of the invention is applicable to all such polypropylenes, as distinguished from polypropylenes in the liquid form or in semiliquid or gel-like forms, such as are used as greases and waxes.

The stabilizer system of the invention is applicable to polypropylenes prepared by any of the various procedures, for the molecular weight and tacticity are not factors affecting this stabilizer. Isotactic polypropylene, available commercially under the trade names Profax, Escon and Olefane and having a softening or hot-working temperature of about 350° F., is an example of a sterically regular polypropylene polymer.

Mixtures of polypropylene with other compatible polymers and copolymers of propylene with copolymerizable monomers also can be improved in accordance with this invention. For example, mixtures of polyethylene and polypropylene, and copolymers of propylene and ethylene which contain a sufficient amount of propylene to present the instability problem that is resolved by the compounds of the invention, may be improved by the addition of one or more of the compounds of the invention, alone or in combination with other polypropylene stabilizers.

The stabilizer systems of the invention may also be used with polyethylene, and with polyolefins higher than polypropylene, such as polybutylene and polyisobutylene.

The stabilizer mixtures of the invention and stabilizer systems including the same are incorporated in the polymer in suitable mixing equipment, such as a mill or a Banbury mixer. If the polypropylene has a melt viscosity which is too high for the desired use, the polypropylene can be worked until its melt viscosity has been reduced to the desired range before addition of the stabilizer. However, polypropylenes in a range of workable melt viscosities are now available. Mixing is continued until the mixture is substantially uniform. The resulting composition is then removed from the mixing equipment and brought to the size and shape desired for marketing or use.

The stabilized polypropylene can be worked into the desired shape, such as by milling, calendering, extrusion or injection molding or fiberforming. In such operations, it will be found to have a considerably improved resistance to reduction in melt viscosity during the heating, as well as a better resistance to discoloration and embrittlement or aging and heating.

The following Examples in the opinion of the inventors represent preferred embodiments of the process for preparation of the stabilizer mixtures in accordance with the invention.

EXAMPLE I

Pentaerythritol tetrakis (3-mercaptopropionate) was reacted with a mixture of α-olefins containing from twenty-four to over thirty carbon atoms having an average molecular weight of 456 as determined by iodine number.

Into a 300 ml round-bottom flask equipped with stirrer, thermometer and dropping funnel there was charged 48.9 g (0.1 mole) of pentaerythritol tetrakis (3-mercaptopropionate). The temperature was brought to 70° C, and 191.5 g (0.42 mole) of liquefied α-olefin mixture composed of α-olefins having from twenty-four to thirty carbon atoms was added over a fourteen minute period. Tertiary-butyl-peroxyneodecanoate (Esperox 33M, 2.4 g) was added, and the reaction mixture brought to 102° C, and held in the range from 102 to 114° C for 5 hours. The reaction mixture was then cooled. A white waxy solid was obtained, 241 g which contained 0.56% by weight SH as measured by analysis of the residual mercaptan groups SH by way of potassium triiodide titration. This showed that 89.7% of the mercaptan had reacted.

The waxy white solid product was recrystallized twice from a 2:1 by volume mixture of methanol and toluene. A white solid was recovered, melting at 70 to 85° C. Titration with potassium triiodide indicated 0.36% by weight SH or 93.5% of this material was reaction product.

EXAMPLE II

Into a 300 ml round-bottom flask equipped with stirrer and thermometer, was charged 48.9 g (0.1 mole) of pentaerythritol tetrakis (3-mercaptopropionate) and 191.5 g (0.42) mole of liquefied α-olefin mixture having an average molecular weight of 456, composed of α-olefins having from twenty-four to over thirty carbon atoms. The mixture was then brought to 82° C. Tertiary butyl peroxyneodecanoate (2.4 g, Esperox 33 M) was then added over a 4.5 hour period, maintaining the temperature within the range from 80 to 90° C, so as to keep the reaction temperature below the decomposition temperature of the tertiary butyl peroxyneodecanoate, which is 96° C, while retaining a liquid reaction mixture. Titration of a sample of the reaction mixture for the remaining mercapto groups SH showed 0.95% by weight SH which indicated that 85.8% of the mercaptan groups had reacted at the end of 4.5 hours.

An additional 2.4 g of tertiary butyl peroxyneodecanoate was then added, and the flask was heated for a further four hours. This reduced the residual mercaptans to 0.78% SH so that 86.9% of the mercaptan had reacted. The solid that was recovered was a brittle, white wax.

20 g of this material was heated with 0.2 g of tertiary butyl peroxybenzoate (Esperox 10), and heated cautiously to 100° C, but no decomposition of the peroxide was noted. The mixture was brought to 150° C, but still no decomposition of peroxide was noted. A sample of this mixture was titrated with potassium triiodide, and it was found to contain 0.13% SH so that 97.6% of the mercaptan groups SH had reacted.

The reaction product was a yellowish wax, having a melting range from 77 to 87° C.

EXAMPLE III

A 300 ml round-bottom flask equipped with stirrer, thermometer and dropping funnel was charged with 191.5 g (0.42 mole) of an α-olefin mixture composed of α-olefins having from twenty-four to over thirty carbon atoms and an average molecular weight of 456. To this mixture was added tertiary butyl peroxybenzoate (Esperox 10, 1.2 g) and the temperature of the mixture was then brought to 99.8° C. Pentaerythritol tetrakis (3-mercaptopropionate) 48.9 (0.1 mole) was then added, over a one hour twenty-five minute period. The temperature was held at 115° C for 1 hour and 15 minutes, and then raised to 150° C for 10 minutes.

The reaction mixture remained in two phases, indicating that the reaction was incomplete. An additional 1.2 g of tertiary butyl peroxybenzoate was then added, and the reaction continued at 140° C for another 40 minutes. Then, 4.8 g of tertiary butyl peroxybenzoate was added over a fifteen minute period, whereupon a one-phase reaction mixture resulted.

Titration of a sample of the reaction mixture with potassium triiodide indicated 1.24 weight % of SH showing that 77% of the mercaptan groups SH had reacted. After reaction for an additional one and one-half hours at 140° C a sample titrated 1.13% SH showing that the 79% of the mercaptan groups had reacted. The cooled product was a white wax.

EXAMPLE IV

A 300 ml found-bottom flask equipped with stirrer, thermometer and dropping funnel was charged with 48.9 g (0.1 mole) of pentaerythritol tetrakis (3-mercaptopropionate). The material was heated to 70° C, and 156.2 g (0.42 mole) of liquefied α-olefin mixture composed of twenty-four to twenty-eight carbon atom α-olefins having an average molecular weight of 372 was added over a twenty minute period, together with tertiary butyl peroxyneodecanoate (Esperox 33 M, 2.1 g) while retaining the reaction temperature within the range from 79 to 90° C. The temperature was then brought to 110 to 115° C, and held there for five hours. Titration of a sample of the reaction product with potassium triiodide for remaining mercaptan groups from 0.5 weight % SH and showed that 92.2% of the mercaptan groups had reacted. A white waxy solid reaction product was obtained.

50 g of this reaction product was dissolved in 100 g of hot heptane. The hot solution was filtered, to remove about 1 g of solid material, and then cooled. The resulting waxy slurry yielded a solid material which was recrystallized from heptane, and then melted at 66 to 73° C and titrated to show 0.44% SH.

EXAMPLE V

Into a 300 ml round-bottom flask was charged 48.9 g (0.1 mole) of pentaerythritol tetrakis (3-mercaptopropionate) and 156.2 g (0.42 mole) of an α-olefin mixture composed of α-olefins having from twenty-four to twenty-eight atoms. The resulting mixture was brought to 70° C, whereupon 2 g tertiary butyl peroxyneodecanoate was added over forty five minutes. A further 2 g tertiary butyl peroxyneodecanoate was added over five minutes, and heating continued while maintaining the reaction temperature within the range from 70.2 to 102° C. At the end of 3 hours and 40 minutes, analysis with potassium triiodide showed 0.27% SH which meant that 95.7% of the mercaptan groups SH had reacted.

The reaction mixture was held at 102° C to a total time of 4 hours and 12 minutes, and then cooled to 84° C over 20 minutes. A further 1 g tertiary butyl peroxyneodecanoate was then added, and heating continued over a period of 1 hour and 15 minutes, while holding the temperature within the range from 82° to 84° C. At the end of this time, analysis with potassium triiodide showed 0.17% SH which meant that 97.4% of the mercaptan groups SH had now reacted. The mixture was then brought to 115° C to destroy the remaining catalyst, and then cooled. A crude waxy material was recovered, which was recrystallized from heptane. After filtering, the product was vacuum-stripped at 100° C to remove solvent. The cooled residue was found to melt over the range of from 71° to 75° C, after recrystallization. Before recrystallization, the melting temperature range was from 65° to 73.5° C.

EXAMPLE VI

A 300 ml round-bottom flask equipped with stirrer, thermometer and dropping funnel was charged with 48.9 g (0.1 mole) of pentaerythritol tetrakis (3-mercaptopropionate). The material was then heated to 60° C while 126.4 g (0.42 mole) of liquefied technical α-eicosene (301 molecular weight as determined by iodine number) was added from the dropping funnel over a one-half hour period, together with 1.75 g tertiary butyl peroxyneodecanoate. About half the catalyst was added at the beginning of the olefin addition, and the remainder was added together with the olefin over a one-half hour period. The temperature was then raised to 100° C, and held there for five hours.

Analysis of the reaction product by potassium triiodide titration found 0.47 weight % SH which showed that 93.7% of the mercaptan groups SH had reacted. A white waxy material was obtained. This was washed several times with a 2:1 by volume mixture of methanol and toluene. The solvent was highly soluble in the product, and a slurry was formed on cooled and filtered, and the resulting product recrystalized from a 2:1 by volume mixture of toluene and methanol. A white powder was obtained, which melted over the range from 60° to 73° C and titrated 0.24% by weight SH.

EXAMPLE VII

A 300 ml found-bottom flask equipped with stirrer and thermometer was charged with 48.9 g (0.1 mole) of pentaerythritol tetrakis 3-(mercaptopropionate) and 126.4 g (0.42) mole of liquefied α-olefin mixture composed of olefins having from 20 to 24 carbon atoms and 301 average molecular weight. The two-phase mixture was heated to 81° C, and 1.8 g tertiary butyl peroxyneodecanoate was then added, dropwise, so that the temperature never exceeded 115° C, at the approximate rate of a drop a minute. A single phase was obtained in 17 minutes at 112° C, and the peak temperature, 115° C was reached in 20 minutes. The addition was over a 35 minute period, at the end of which time the reaction temperature was 109° C.

After 2 hours at 102° to 111° C, a sample of the product was titrated with potassium triiodide (0.26 weight % SH) and it was found that 96.8% of the mercaptan groups SH had reacted. An additional 0.9 g of tertiary butyl peroxyneodecanoate (Esperox 33 M) was added, and the heating continued for an additional two hours at 114° C. By the end of this time, 97.9% of the mercaptan groups had reacted as shown by a 0.16 weight % SH content.

A third addition of 1.8 g of tertiary butyl peroxyneodecanoate was made, over twenty minutes. The total catalyst amounted to 2.5% of the batch weight. After heating an additional 1 hour and 20 minutes at 102° to 111° C, analysis with potassium triiodide showed 0.09% SH which meant that 98.8% of the mercaptan groups had reacted. A white, waxy product was obtained.

50 g of this product was recrystallized from 100 g of heptane. The crude product had a melting range from 62° to 66.5° C. The recrystallized product melted over the range from 66° to 68° C and titrated 0.08% SH.

EXAMPLE VIII

A 300 ml found-bottom flask equipped with stirrer, thermometer and dropping funnel was charged with 36.7 g (0.075 mole) of pentaerythritol tetrakis (3-mercaptopropionate). This was heated to 75° C, and 180.6 g (0.6 mole) of liquefied α-olefin mixture composed of α-olefins having from twenty to twenty-four carbon atoms was added over a 35 minute period. Tertiary butyl peroxyneodecanoate, 2.2 g, was added at the beginning of the olefin addition.

The peak temperature of 81° C was reached about half way through the addition of the α-olefin. The temperature was then raised to 100° C for another 2.25 hours, after which analysis with potassium triiodide showed 0.05% by weight SH which meant that 99% of the mercaptan groups SH had reacted. On cooling, a white wax was obtained.

EXAMPLES IX to XI

In a three necked 1-liter flask equipped with stirrer, thermometer and additional funnel, 169.5 g (0.33 mole) of tris hydroxyethyl isocyanurate tris(3-mercaptopropionate) was reacted with the following α-olefins, using the catalyst noted:

EXAMPLE IX:

264.6 g octadecene (1.05 mole)
4.34 g tertiary butyl peroxyneodecanoate (Esperox 33 M)

EXAMPLE X 235.2 g hexadecene (1.05 mole)
4.04 g tertiary butyl peroxyneodecanoate (Esperox 33 M)

EXAMPLE XI 109.2 g styrene (1.05 mole)
2.87 g tertiary butyl peroxyneodecanoate (Esperox 33 M)

In each case, the ester was brought to 75° C, and then a mixture of the olefin and catalyst was added slowly from a dropping funnel. The reaction was exothermic, and the maximum temperature reached during the addition was approximately 125° C. After all of the materials had been added and the exothermic heat of reaction declined, the temperature was held at 100° C for 5 hours. The reaction mixtures were then allowed to cool.

The solid materials recovered were brought to their melting points, and recrystallized in hexane, filtered, and then dried in a desiccator. The reaction product from Example XI was a hazy, viscous liquid; refractive index 1.5675, specific gravity 1.43. The Example IX recrystallized material had a melting range of from 78° to 82° C and analyzed 0.42% SH; the Example X material a melting range of from 75° to 79° C.

EXAMPLES XII to XIV

In a one liter three-necked flask equipped with stirrer, thermometer and addition funnel, there was charged 122 g (0.25 mole) of pentaerythritol tetrakis (3-mercaptopropionate). To the ester there was then added one of the following α-olefins, using the catalyst noted:

EXAMPLE XII 109.2 g styrene (1.05 moles)
2.31 g tertiary butyl peroxyneodecanoate (Esperox 33 M)

EXAMPLE XIII 138.6 g dicyclopentadiene (1.05 moles)
2.56 g tertiary butyl peroxyneodecanoate (Esperox 33 M)

EXAMPLE XIV 264.4 g octadecene (1.05 moles)
3.86 g tertiary butyl peroxyneodecanoate (Esperox 33 M)

The ester was brought to 75° C, and the mixture of olefin and catalyst then slowly added from the addition funnel. Heat of reaction brought the reaction mixture to within the range from about 115 to about 120° C. When all of the mixture of olefin and catalyst had been added, the reaction mixture was heated for five more hours at 100° C. The products were allowed to cool.

The product from Example XIV was a solid, while the reaction products from Examples XII and XIII were liquids.

The solid material was reheated to its melting point and recrystallized in hexane, filtered and dried in a desiccator under vacuum. It was found to melt over a range from 64° to 66° C and analyzed 0.13% SH.

The liquid material from Example XII had a specific gravity of 1.30 and a refractive index of 1.5719. The liquid reaction product from Example XIII had a specific gravity of 1.43 and a refractive index of 1.5574, and analyzed 0.42% SH.

EXAMPLES XV to XVIII

In a one liter three-necked equipped with stirrer, thermometer and addition funnel, there was charged 80.52 g of dipentaerythritolhexa 3-mercaptopropionate (0.167 mole). This ester was then reacted with one of the following α-olefins using the catalyst noted:

EXAMPLE XV 264.6 g octadecene (1.05 moles)
3.4 g tertiary butyl peroxyneodecanoate (Esperox 33 M)

EXAMPLE XVI 235.2 g hexadecene (1.05 moles)
3.16 g tertiary butyl peroxyneodecanoate (Esperox 33 M)

EXAMPLE XVII 109.2 g styrene (1.05 moles)
1.90 g tertiary butyl peroxyneodecanoate (Esperox 33 M)

EXAMPLE XVIII 138.6 g dicyclopentadiene
2.2 g tertiary butyl peroxyneodecanoate (Esperox 33 M)

In each case, the ester was brought to 75° C, and the addition of a mixture of hydrocarbon and catalyst was then begun. Exothermic heat of reaction was liberated, and the reaction mixtures reached from 110° to 115° C. After the exothermic heat of reaction had subsided, the reaction mixtures were heated at 100 ° C for 5 hours. The products were then allowed to cool overnight.

The reaction products of Examples XV and XVI were solids. The reaction mixtures of Examples XVII and XVIII were liquids. That of Example XVII was a yellowish, hazy, relatively fluid liquid, while that of Example XVII was a thick, hazy brown liquid.

The solid material of Example XV melted over a range of 46° to 52° C after being heated to its melting point and recrystallized from methanol, filtered, and dried in a desiccator overnight. After similar purification, the reaction product of Example XVI melted over a range of from 45 to 51° C.

EXAMPLE XIX

Pentaerythritol tetrakis (3-mercaptopropionate) 122 g (0.25 mole) was warmed to 75° C with stirring and a solution of 4 g tertiarybutylperoxyenodecanoate in 224 g 1-hexadecene added from a dropping funnel during 1 hour. The temperature gradually rose to 95° C and was held at 95° to 100° C for 6 hours. The product was cooled to 60° C and 500 c.c. hexane added. On cooling to room temperature a white solid precipitated. This collected and dried weighed 184.0 g for a 53% of theoretical yield of addition product, m.p. 44° to 49° C.

More solid product was obtainable from the hexane mother liquors.

EXAMPLE XX

Pentaerythritol tetrakis (3-mercaptopropionate) was reacted with a mixture of α-olefins containing sixteen to eighteen carbon atoms with lauroyl peroxide catalyst.

Pentaerythritol tetrakis (3-mercaptopropionic acid ester) 48.6 g (0.1 mole) was charged into a 250 ml four-necked flask equipped with a sealed mechanical stirrer, thermometer, dropping funnel and reflux condenser, and warmed to 70° C. 97.0 g (0.42 mole) of α-olefin (Mitsubishi Chemical Co. DIALEN 168) containing dissolved lauroyl peroxide 1.3 g was added dropwise. Reaction started immediately. Because violent exothermic heating occurred, the rate of addition was controlled so as not to exceed 120° C. About two hours was taken for addition. After addition, the temperature was maintained at 110°–115° C for 6 hours. The mixture was cooled to room temperature, taken from the flask, and crystallized from toluene-methanol system to obtain a white crystalline powder of 134.3 g.

In the IR spectrum, a broad absorption of 2560 cm$^{-1}$ characteristic of the mercapto starting material and sharp absorption of 1640 cm$^{-1}$ by carbon-carbon double bonding of α-olefin starting material were completely disappeared. Sulfur content measured by oxygen flask combustion method was 8.7%. Melting point was 62° to 64° C.

EXAMPLE XXI

Trimethylolpropane tris (3-mercaptopropionate) was reacted with a mixture of $C_{12}$–$C_{14}$ α-olefins and dicumyl peroxide catalyst.

1, 1, 1-trimethylolpropane tris (3-mercaptopropionic acid ester) 39.2 g (0.1 mole), α-olefin (DIALEN 124) 55.5 g (0.31 mole), toluene 100 ml and dicumyl peroxide 0.3 g were charged into a four-necked flask of 250 ml, equipped with a sealed mechanical stirrer, thermometer and reflux condenser, then heated up while stirring. When the mixture reached 80° C, dissolution of peroxide occurred and the addition reaction started. The reaction was exothermic. The reflux of toluene was controlled so as to be quieted by cooling with water. The reflux was continued for 8 hours, then heated to 110° C and reacted at this temperature for 2 hours. After the reaction, toluene was removed by distilling under reduced pressure and the product was obtained as white waxy matter 90.7 g.

After an impurity was removed by liquid chromatography, and the IR spectrum of the product measured, the broad absorption of 2560 cm$^{-1}$ by the mercapto group and sharp absorption of 1640 cm$^{-1}$ by the carbon-carbon double bond of the α-olefin had completely disappeared. The sulfur content measured by the usual way was 10.1%. Melting point was 50 to 54° C.

EXAMPLE XXII

Dipentaerythritol hexakis (3-mercaptopropionate) was reacted with a mixture of α-olefins having twenty to twenty-eight carbon atoms and t-butylcumyl peroxide catalyst.

Dipentaerythritol hexa (3-mercaptopropionic acid ester) 73.8 g (0.1 mole), xylene 200 ml and α-olefin (DIALEN 208) 192.4 g (0.60 mole) were charged into 1000 ml flask and warmed up to 60° C. 1.3 g of t-butylcumyl peroxide was added and cautiously heated to the reflux temperature (145° C) of the medium. After the reaction at reflux temperature for about three hours, a second portion of t-butylcumyl peroxide (1.3 g) was added and reacted in the same way and, a third addition of peroxide and similar reaction were carried out. The solvent was removed by vacuum stripping and the melted product removed, cooled, and solidified. The crude yield was 258.1 g. The crude product was pulverized, dissolved in warm hexane 200 ml, and recrystallized then to obtain 245.3 g of white crystals.

In the IR spectrum, the absorption of 2560 cm$^{-1}$ by the mercapto group and the absorption of 1640 cm$^{-1}$ by the carbon-carbon double bond of α-olefin had completely disappeared, and the sulfur content measured by the usual way was 7.2%. The melting point was 68° to 72° C.

EXAMPLE XXIII

The 3-mercaptopropionate ester of tris (2-hydroxyethyl) isocyanurate was reacted with a mixture of α-olefins having sixteen to eighteen carbon atoms and lauryl peroxide catalyst.

Tris 2-(3-mercaptopropionyloxy) ethyl isocyanurate 105 g (0.2 mole) was weighed into a flask and warmed up to 70° C. A solution of dissolved lauroyl peroxide 2.5 g in α-olefin (DIALEN 168) 141 g was added dropwise. As the reaction system was exothermic, the rate of addition was controlled not to exceed 120° C in the mixture. After the addition the mixture was maintained at 110 to 115° C for 6 hours, cooled to room temperature, solidified, taken from flask, and recrystallized to obtain 235 g of white crystalline powder. When the white powder was dissolved in chloroform and analyzed by gel permeation chromatography, one peak was obtained at retention volume corresponding to molecular weight of about 1220.

The IR spectrum of the product had no absorption of 2560 cm$^{-1}$ (mercapto group) and absorption of 1640 cm$^{-1}$ (carbon-carbon double bonding of α-olefin). Sulfur content measured by oxygen flask combustion method was 7.75%. Melting point was 72° to 76° C.

EXAMPLE XXIV

A 300 ml round-bottom flask equipped with stirrer and thermometer was charged with 73.4 g (0.15 mole) of pentaerythritol tetrakis (3-mercaptopropionate) and 45.2 g (0.15 mole) of technical liquefied α-eicosene. The two-phase mixture was heated to 86° C, and 1.2 g tertiary butyl peroxyneodecanoate was then added, dropwise, at the approximate rate of two drops a minute for 15 minutes and the remainder rapidly during 5 minutes. Since single phase was not obtained the mixture was warmed to 100° C, another 1.2 g portion of tert-butylperoxyneodecanoate added during five minutes, and heating continued for 2 hours, at the end of which time the reaction temperature was 109° C. The reaction mixture still showed two liquid phases but the quantity of lighter phase had increased and the heavier phase diminished to a very small amount. On cooling, however, there appeared two distinct phases, a white wax that by potassium triiodide titration contained 5.91% SH and a pale yellow transparent gel that titrated 22.6% SH. The mixture was reheated to melt the solids transferred to a separatory funnel and kept at 60° C until the layers could be separately drawn off. The upper layer (5.91% SH) weighed 81.5 g and the lower layer weighed 37.7 g.

5 g of the upper phase product was recrystallized from 20 g of heptane. About 0.2 g failed to dissolve at the boil. The solution on cooling gave 2.75 g of white recrystallized product, melting point 59° to 66° C, titrated 4.58% SH.

EXAMPLE XXV

A 300 ml round-bottom flask equipped with stirrer and thermometer was charged with 48.9 g (0.1 mole) of pentaerythritol tetrakis (3-mercaptopropionate) and 60.2 g (0.2 mole) of liquefied technical α-eicosene. The twophase mixture was heated to 91° C, and 1.8 g tertiary butyl peroxyneodecanoate was then added, dropwise, so that the temperature never exceeded 93° C, during 25 minutes. Heating was then continued for 1 hour at 90° and one hour at 110° to 114° C. A single phase was obtained after this treatment and a sample titrated 5.85% SH. Continued heating for 2 hours 45 minutes gave 105 g of waxy product which titrated 5.5% SH.

The following Examples in the opinion of the inventors represent preferred embodiments of polyolefin compositions containing the stabilizer mixtures in accordance with the invention.

EXAMPLE 1

A polypropylene composition was prepared having the following formulation:

|  | Parts By Weight |
|---|---|
| Polypropylene (Profax 6501) | 100 |
| 1,1,3-tris (2-methyl-4-hydroxy-5-t-butylphenyl) butane | 0.15 |
| Stabilizer | 0.5 |

The stabilizers employed are shown in Table I below. As controls comparing known stabilizers, one composition (Control A) was prepared using distearyl thiodipropionate as the stabilizer, and another composition (Control B) was prepared using the thiodipropionic acid ester of 1,4-cyclohexanedimethanol and stearyl alcohol, in accordance with Tholstrup U.S. Pat. No. 3,378,516. The stabilizer in accordance with the invention was that of Example XIX, the reaction product of pentaerythritol 3-mercaptopropionate ester with hexadecene-1.

The composition was prepared by dispersing the stabilizer by hand-stirring in the powdered previously unstabilized polypropylene, Profax 6501, which has a reduced specific viscosity RSV of 3.0, a melt index of 0.4 ASTM D1238-57T at 190° C. Profax 6501 contains a minute quantity of 2,6-di-t-butyl-p-cresol for protection during shipment and storage only (about 9.01%). This antioxidant volatilizes during hot processing and imparts no heat stability. The mixture was then placed on a two-roll mill and fluxed for five minutes at 170± 2° C. Pieces cut from the milled sheet were then compression molded four minutes at 200± 3° C to form smooth panels 0.5 mm thick. These were used for the heat-ageing test which was carried out as follows:

The samples made as described are heated flat on aluminum foil in an air-circulating oven at 150° C. Samples are removed daily, and examined for cracking and powdering, either of which constitutes failure. The number of days to failure at 150° C is then noted. Color is noted at the end of three days if the sample has not yet failed.

For comparison purposes, the color rating of the mixture initially is also noted in the Tables.

The rating for color is in accordance with a scale ranging from 1 to 10, in which a rating of 1 indicates colorless, and a rating of 4, a brown discoloration.

The following results were obtained:

TABLE I

| Example | Thioether Stabilizer | Original Color rating Unexposed | Color Rating After 3 days at 150° C | Days to Failure at 150° C |
|---|---|---|---|---|
|  | NONE | 2 | — | 2 |
| Control A | Distearyl thiodipropionate | 2 | 3 | 55 |
| Control B | Stearyl 1,4-cyclohexanedimethanol thiodipropionate | 2 | 4 | 27 |
| Example 1 | Product of PE-MPA ester with hexadecene-1 | 1 | 2 | 100 |

It is apparent from the above results that the stabilizer mixture in accordance with the invention is far superior to the two prior art stabilizers tested.

EXAMPLE 2

A polypropylene composition was prepared having the following formulation:

|  | Parts by Weight |
|---|---|
| Polypropylene (Profax 6501) | 100 |
| Calcium stearate | 0.15 |
| 1,1,3-tris(2-methyl-4-hydroxy-5-t-butylphenyl) butane | 0.15 |
| Stabilizer | 0.5 |

The stabilizers employed are shown in Table 2 below. As controls comparing known stabilizers, one composition (Control C) was prepared using distearyl thiodipropionate as the stabilizer; another composition (Control D) was prepared using dilauryl thiodipropionate stabilizer and a third composition (Control E) was made with tri ($C_{12}$—$C_{15}$ alkyl) carboxyethylthiosuccinate in accordance with Gilles U.S. Pat. No. 3,909,493. The stabilizer in accordance with the invention was that of Example XIX, from 1-hexadecene and pentaerythritol tetrakis (3-mercaptopropionate) with t-butylperoxyneodecanoate catalyst.

Test samples of each composition are prepared as described in Example 1.

The samples made as described are heated flat on aluminum foil in an air-circulating oven at 150° C. Samples are removed daily, and examined for cracking and powdering, either of which constitutes failure. The number of days to failure at 150° C is then noted. Color is noted at the end of 3 days if the sample has not yet failed.

For comparison purposes, the color rating of the mixture initially is also noted in the Tables.

The rating for color is in accordance with a scale ranging from 1 to 10, in which a rating of 1 indicates colorless, and a rating of 4, a brown discoloration.

The following results were obtained:

TABLE 2

| Example | Thioether Stabilizer | Original Color rating Unexposed | Color Rating After 3 days at 150° C | Days to Failure at 150° C |
|---|---|---|---|---|
| Control C | Distearyl thiodipropionate | 2 | 3 | 50 |
| Control D | Dilauryl thiodipropionate | 2 | 3 | 35 |
| Control E | Tri-($C_{12}$-$C_{15}$ alkyl) carboxyethyl thiosuccinate | 2 | 2 | 42 |
| Example 2 | Example XIX product | 1 | 2 | 73 |

The results show that the stabilizer mixture of this invention is far superior to the prior art stabilizers tested.

EXAMPLES 3-7

A polypropylene composition was prepared having the following formulation:

| | Parts by Weight |
|---|---|
| Polypropylene (Profax 6501) | 100 |
| 1,1,3-tris (2-methyl-4-hydroxy-5-t-butylphenyl) butane | 0.1 |
| Stabilizer | 0.3 |

The stabilizers employed are shown in Table 3 below. As controls one composition (Control F) was prepared without any thioether stabilizer, and another composition (Control G) was prepared using dilauryl thiodipropionate. The stabilizers in accordance with the invention were the products of Examples XX through XXIII and XIV.

The composition was prepared by dispersing the stabilizer by machine grinding for ten minutes in the powdered previously unstabilized polypropylene. Profax 6501 has a reduced specific viscosity RSV of 3.0, a melt index of 0.4 ASTM D1238-57T at 190° C. The mixture was then placed on a two-roll mill and fluxed for five minutes at 170° ± 2° C.

A sheet of 1.0 mm in thickness was prepared by compression molding under the condition of 180° C and 200 kg/cm² for 5 minutes. This sheet was cut to the size of 10 × 20 mm of sample piece and heating test was carried on aluminum foil in a Geer air circulating oven at 160° C under air atmosphere. The time at which more than five pieces of ten were discolored and brittle was taken as the time of failure.

To evaluate blooming, the molded sheet was kept in a clear dustproof glass vessel for twenty days, and then wiped with a black cloth. The degree of material pickup by the cloth was judged visually.

The results are shown in Table 3.

TABLE 3

| Example | Thioether Stabilizer | Days to Failure at 160° C | Bloom |
|---|---|---|---|
| Control F | None | 4 | None |
| Control G | Dilauryl thiodipropionate | 18 | Heavy |
| Example 3 | Product of PE-MPA ester with $C_{16}$-$C_{18}$ olefin mixture, Example XX | 52 | None |
| Example 4 | Product of PE-MPA ester with 1-octadecene, Example XIV | 50 | None |
| Example 5 | Product of trimethylol propane MPA ester with $C_{12}$-$C_{14}$ olefin mixture, Example XXI | 47 | None |
| Example 6 | Product of dipentaerythritol MPA ester with $C_{20}$-$C_{28}$ olefin mixture, Example XXII | 61 | None |
| Example 7 | Product of tris (2-hydroxyethyl-isocyanurate) MPA ester with $C_{16}$-$C_{18}$ olefin mixture, Example XXIII | 51 | None |

The results show the products of this invention capable of providing improved heat stability without the objectional bloom that is obtained with conventional thioether stabilizers.

EXAMPLES 8 to 11

A polypropylene composition was prepared having the following formulation:

| | Parts by Weight |
|---|---|
| Polypropylene (Profax 6501) | 100 |
| Calcium stearate | 0.2 |
| n-octadecyl 3,5-di-t-butyl-4-hydroxy hydrocinnamate | 0.1 |
| Stabilizer | 0.3 |

The composition was prepared by dispersing the stabilizer by machine grinding for ten minutes in the powdered previously unstabilized polypropylene. Profax 6501 has a reduced specific viscosity RSV of 3.0, a melt index of 0.4 ASTM D1238-57T at 190° C. The mixture was then placed on a two-roll mill and fluxed for five minutes at 170° ± 2° C.

A sheet of 1.0 mm in thickness was prepared by compression molding under the condition of 180° C and 200 kg/cm² for five minutes. This sheet was cut to the size of a 10 × 20 mm sample piece, and the heating test was carried on aluminum foil in a Geer air circulating oven at 160° C under air atmosphere. The time at which more than five pieces of ten were discolored and brittle was taken as the time of failure. In addition, the color and odor of the compression molded sheets were observed.

As controls comprising known stabilizers, one composition (Control H) was prepared using dilauryl thiodipropionate as the stabilizer, and another composition (Control J) was prepared using the pentaerythritol ester of 3-n-dodecylmercaptopropionic acid, in accordance with Dexter U.S. Pat. No. 3,758,549. The stabilizers in accordance with the invention were the products of Examples IX, XIV, XX and XXIII.

The pentaerythritol ester of 3-n-dodecylmercaptopropionic acid was prepared following the procedure of Dexter U.S. Pat. No. 3,758,549, Example 4.

To a mixture of 101 g (0.5 mol) of n-dodecyl mercaptan and 0.5 g of NaOCH₃ was added 68.4 g (0.8 mol) of methyl acrylate at 25° to 30° C during about one hour. After the addition the reaction was continued for fifteen hours at 25° to 30° C and 67.0 g of methyl-3-n-dodecylmercaptopropionate was obtained by vacuum distillation (151° to 153° C/0.3 mm Hg). 57.6 g (0.2 mol) of this ester, 6.5 g (0.048 mol) of pentaerythritol and 0.25 g of NaOCH₃ were reacted for seven hours at 100° to 110° C under a nitrogen stream. After cooling to room temperature, toluene was added and the whole was passed through a bed of alumina. 58.0 g of white powder was obtained by adding methanol to the solution, M.P. 45° to 47.5° C, which corresponds closely to the 47° to 49° C melting point given by Dexter for pentaerythritol tetrakis (3-n-dodecylthiopropionate).

The stabilizers employed and results obtained are shown in Table 4 below.

TABLE 4

| Example | Thioether Stabilizer | Original Color Rating | Odor Rating | Days to Fail 160° C |
|---------|---------------------|----------------------|-------------|---------------------|
| Control H | Dilauryl thiodipropionate | 2 (very pale yellow) | slight | 24 |
| Control J | Pentaerythritol ester of 3-n-dodecylmercaptopropionate acid of Dexter No. 3,758,549 | 2-3 (pale yellow) | characteristic objectionable | 28 |
| Example 8 | Product of PE-MPA ester with $C_{16}$-$C_{18}$ olefin mixture Example XX | 1 (colorless) | none | 41 |
| Example 9 | Product of PE-MPA ester with 1-octadecene Example XIV | 1 (colorless) | none | 40 |
| Example 10 | Product of tris-2-hydroxyethyl isocyanurate-MPA ester with 1-octadecene, Example IX | 1 (colorless) | none | 41 |
| Example 11 | Product of tris-2-hydroxyethyl isocyanurate-MPA ester with $C_{16}$-$C_{18}$ olefin mixture Example XXIII | 1 (colorless) | none | 42 |

The superiority of the stabilizers of the invention in the properties of color contribution, odor contribution and heat stability is evident from the above results.

EXAMPLES 12 to 17

Polypropylene compositions were prepared having the following formulations:

| | Parts by Weight |
|---|---|
| Polypropylene (Profax 6501) | 100 |
| 1,1,3-tris(2-methyl-4-hydroxy-5-t-butylphenyl) butane | 0.1 |
| Stabilizer | 0.5 |

The composition was prepared by dispersing the stabilizer by hand-stirring in the powdered previously unstabilized polypropylene, Profax 6501, which has a reduced specific viscosity RSV of 3.0, a melt index of 0.4 ASTM D1238-57T at 190° C. Profax 6501 contains a minute quantity of 2.6-di-t-butyl-p-cresol for protection during shipment and storage only (about 9.01%). This antioxidant volatilizes during hot processing and imparts no heat stability. The mixture was then placed on a two-roll mill and fluxed for 5 minutes at 170° ± 2° C. Pieces cut from the milled sheet were then compression molded 4 minutes at 200° ± 3° C to form smooth panels 0.5 mm thick. These were used for the heat-ageing test which was carried out as follows:

The samples made as described are heated flat on aluminum foil in an air-circulating oven at 150° C. Samples are removed daily, and examined for cracking and powdering, either of which constitutes failure. The number of days to failure at 150° C is then noted. The stabilizers used and results obtained are shown in Table 5 below. The stabilizers in accordance with the invention were crude and recrystallized products of Examples I, V and VI.

TABLE 5

| Example | Thioether Stabilizer | Days to failure 150° C oven |
|---------|---------------------|-----------------------------|
| Control K | None | 11 |
| Example 12 | Pentaerythritol MPA ester + $C_{24}$ to over $C_{30}$ olefin product, crude, 0.56% SH (Example I) | 48 |
| Example 13 | Pentaerythritol MPA ester + $C_{24}$ to over $C_{30}$ olefin product, recrystallized, 0.36% SH (Example I) | 44 |
| Example 14 | Pentaerythritol MPA ester + $C_{24}$ to $C_{28}$ olefin product, crude, 0.27% SH (Example V) | 90 |
| Example 15 | Pentaerythritol MPA ester + $C_{24}$ to $C_{28}$ olefin product, recrystallized, 0.17% SH (Example V) | 106 |
| Example 16 | Pentaerythritol MPA ester + 1-eicosene, crude, 0.47% SH (Example VI) | 106 |
| Example 17 | Pentaerythritol MPA ester + 1-eicosene, recrystallized, 0.24% SH (Example VI) | 97 |

These results show that the crude reaction products obtained in accordance with this invention are approximately as effective as purified samples.

EXAMPLES 18 and 19

A polypropylene composition was prepared with thioethers of this invention as the only added stabilizer, as follows:

| | Parts by Weight |
|---|---|
| Polypropylene | 100 |
| Stabilizer | 0.5 |

The composition was prepared by dispersing the stabilizer by hand-stirring in the powdered previously unstabilized polypropylene, Profax 6501, which has a reduced specific viscosity RSV of 3.0, a melt index of 0.4 ASTM D1238-57T at 190° C. Profax 6501 contains a minute quantity of 2,6-di-t-butyl-p-cresol for protection during shipment and storage only (about 9.01%). This antioxidant volatilizes during hot processing and imparts no heat stability. The mixture was then placed on a two-roll mill and fluxed for 5 minutes at 170° ± 2° C. Pieces cut from the milled sheet were then compression molded four minutes at 200° ± 3° C to form smooth panels 0.5 mm thick. These were used for the heat-ageing test which was carried out as follows:

The samples made as described are heated flat on aluminum foil in an air-circulating oven at 150° C. Samples are removed daily, and examined for cracking and powdering, either of which constitutes failure. The number of days to failure at 150° C is then noted. The stabilizers used and results obtained are shown in Table 6 below. The stabilizers in accordance with this invention were crude and recrystallized products of Example VI.

TABLE 6

| Example | thioether Stabilizer | Days to failure 150° C oven |
|---|---|---|
| Control L | None | Less than 1 |
| Control M | Dilauryl thiodipropionate | 3 |
| Example 18 | Pentaerythritol MPA ester + 1-eicosene product, crude 0.47% SH (Example VI) | 8 |
| Example 19 | Pentaerythritol MPA ester + 1-eicosene product, recrystallized, 0.24% SH (Example VI) | 7 |

The stabilizing effectiveness of the thioethers of the invention in the absence of other additives is quite remarkable, compared to that of known thioether stabilizers.

EXAMPLES 20 and 21

Polypropylene sheets of 0.5 mm thickness were prepared for heat and light stability testing according to the following formulation:

| | Parts by Weight |
|---|---|
| Unstabilized polypropylene resin | 100 |
| 1,1,3-tris-(2-methyl-5-t-butyl-4-hydroxyphenyl) butane | 0.1 |
| Thioether stabilizer | 0.3 |

The composition was prepared by dispersing the stabilizer by machine grinding for ten minutes in the powdered previously unstabilized polypropylene. Profax 6501 has a reduced specific viscosity RSV of 3.0, a melt index of 0.4 ASTM D1238-57T at 190° C. The mixture was then placed on a two-roll mill and fluxed for five minutes at 170°± 2° C.

A sheet of 1.0 mm in thickness was prepared by compression molding under the condition of 180° C and 200 kg/cm² for five minutes. This sheet was cut to the size of 10 × 20 mm of sample piece and the heating test was carried on aluminum foil in a Geer air circulating oven at 160° C under air atmosphere. The time at which more than five pieces of ten were discolored and brittle was taken as the time of failure. The yellowness of the sheets before and after irradiation for 64 hours with fluorescent light was measured by Hunter colorimeter. The results are shown in Table 7.

The results show the products of the invention provide better heat stability coupled with minimal discoloration on exposure to light compared to known thioether stabilizers.

EXAMPLES 22 and 23

Stabilized sheets 12 mm thick of high density polyethylene resin 100 parts by weight and thioether stabilizer 0.15 part were prepared by kneading on mixing rolls at 150° C for 5 minutes, and then compression molded at 150° C and 180 kg/cm² for five minutes. Test pieces 10 × 20 mm were cut off from this sheet and tested for heat stability by heating on aluminum foils in a Geer air circulating oven at 150° C in an air atmosphere.

Ten pieces were used of each sample and the time when more than five pieces were discolored or waxy, was taken as the time of failure.

The results are shown in Table 8.

TABLE 8

| Example | Thioether Stabilizer | 150° C oven Days to failure |
|---|---|---|
| Control N | None | 8 |
| Control P | Pentaerythritol ester of 3-n-dodecyl-mercaptopropionic acid of Dexter Pat. No. 3,758,549 | 13 |
| Example 22 | $C_{16}$–$C_{18}$ olefin/pentaerythritol 3-mercaptopropionate product (Example XX) | 20 |
| Example 23 | 1-octadecene/tris (hydroxyethyl-isocyanurate) 3-mercaptopropionate product (Example IX) | 20 |

Thioether stabilizers of the invention provide a significant improvement over a known thioether stabilizer or no thioether stabilizer in protecting high density polyethylene against heat deterioration.

EXAMPLES 24 to 27

Low density polyethylene was compounded with stabilizers for heat stability testing as follows:

Into a 5 g portion of finely powdered polyethylene (Microthene F) was dispersed by hand mixing 0.2 g di-t-butyl-p-cresol antioxidant and 0.2 g thioether stabilizer. Pellets of polyethylene (Bakelite DYNK 95 g) were fused and banded on a two-roll mill at 105° to 110° C. The product of polyethylene powder and stabilizers then added, homogenized by milling for three minutes and sheeted off 0.75 mm thick. Strips for oven testing were cut from the milled sheet and exposed in an air circulating oven at 190° C until any of several failure symptoms were observed. Signs of failure were yellow, brown or gray discoloration, or the appearance of a waxy deposit covering the initially shiny samples.

The results obtained are shown in Table 9.

TABLE 7

| Example | Thioether Stabilizer | 160° oven Days to failure | Hunter Yellowness 64 hr fluorescent light exposure Before | After |
|---|---|---|---|---|
| Control L | Distearyl thiodipropionate | 20 | 0.11 | 0.21 |
| Control M | Pentaerythritol ester of 3-n-dodecylmercaptopropionic acid of Dexter Pat. No. 3,758,549 | 34 | 0.10 | 0.18 |
| Example 20 | $C_{16}$–$C_{18}$ olefin/pentaerythritol 3-mercaptopropionate product Example XX | 47 | 0.10 | 0.12 |
| Example 21 | 1-octadecene/tris(hydroxyethyl isocyanurate) 3-mercaptopropionate product Example IX | 46 | 0.09 | 0.11 |

TABLE 9

| Example | Thioether Stabilizer | 190° C oven test Description and time of Failure |
|---|---|---|
| Control Q | None | Waxy deposit at one hour |
| Control R | Dilauryl thiodipropionate | Yellow at forty-five minutes |
| Example 24 | Product of pentaerythritol 3-mercaptopropionate with 1-octadecene (Example XIV) | Slight brown spotting at one hour thirty minutes |
| Example 25 | Product of tris(hydroxyethyl) isocyanurate)3-mercaptopropionate with 1-octadecene (Example IX) | Waxy deposit at two hours |
| Example 26 | Blend of distearyl thiodipropionate with 2:1 molar ratio 1-eicosene PE-MPA ester product (Example XXV) proportions 82:18 by weight | slight brown spotting at one hour forty-five minutes |
| Example 27 | Blend of 4% to 1 molar ratio 1-eicosene/PE-MPA ester product (Example VI) with 2:1 molar ratio product (Example XXV) proportions 82:18 by weight | Slight brown spotting at two hours |

Since in this polymer the conventional thioether detracts from heat stability, the considerable positive contribution by the stabilizers of this invention is surprising and unexpected.

Having regard to the foregoing disclosure, the following is claimed as inventive and patentable embodiments thereof:

1. A stabilizer mixture for enhancing the resistance of poly-α-olefins to deterioration in physical properties when exposed to light, air and heat, comprising the product of the reaction of an α-olefin having the formula:

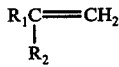

wherein:
R$_1$ and R$_2$ are selected from the group consisting of hydrogen, monovalent hydrocarbon groups having from one to about thirty carbon atoms, and such groups including at least one inert substituent selected from oxyether, thioether, hydroxyl and polysulfide groups; with a multifunctional ester of a mercaptocarboxylic acid of a polyhydric alcohol having from one to eight mercapto groups and from one to eight carboxylic acid ester groups; said ester having the formula:

wherein:
m is the number of HS groups, and is a number from one to about four;
n is the number of mercapto groups and is a number from three to about eight;
R is an organic group derived from a polyhydric alcohol of the formula R'(OH)$_p$ where p is a number from three to about eight; and
Z is selected from the group consisting of bivalent alkylene radicals carrying at least one HS group in a position alpha or beta to a COOR group, and such radicals containing at least one additional group selected from carboxylic acid, carboxylic ester, and mercapto groups; the ester and the α-olefin being in a molar ratio ester: α-olefin within the range from 1:1 to 1:8; at least one mercapto group of the multifunctional ester being extinguished in the course of the reaction, said reaction product containing thioether groups and carboxylic acid ester groups, with the residue of the multifunctional ester being attached to the α-olefin, together with unreacted starting materials and reaction by-products.

2. A stabilizer mixture according to claim 1, in which the mercaptocarboxylic acid is 3-mercaptopropionic acid.

3. A stabilizer mixture according to claim 1, in which the polyhydric alcohol is pentaerythritol.

4. A stabilizer mixture according to claim 1, in which the polyhydric alcohol is tris (hydroxyethyl) isocyanurate.

5. A stabilizer mixture according to claim 1, in which the polyhydric alcohol is tris (methylol) propane.

6. A stabilizer mixture according to claim 1, in which the α-olefin is hexadecene.

7. A stabilizer mixture according to claim 1, in which the α-olefin is octadecene.

8. A stabilizer mixture according to claim 1, in which the α-olefin is eicosene.

9. A stabilizer mixture according to claim 1, comprising an antioxidant.

10. A stabilizer mixture according to claim 9, in which the antioxidant is a phenol.

11. A stabilizer mixture according to claim 9, in which the antioxidant is an organic phosphite.

12. A process for preparing a stabilizer mixture for poly-α-olefins, which comprises reacting an α-olefin having the formula:

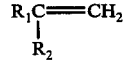

wherein:
R$_1$ and R$_2$ are selected from the group consisting of hydrogen, monovalent hydrocarbon groups having from one to about thirty carbon atoms, and such groups including at least one inert substituent selected from oxyether, thioether, hydroxyl and polysulfide groups, with a multifunctional ester of a mercaptocarboxylic acid and a polyhydric alcohol; said ester having the formula:

wherein:

$m$ is the number of HS groups, and is a number from one to about four;

$n$ is the number of mercapto groups and is a number from three to about eight;

R is an organic group derived from a polyhydric alcohol of the formula $R'(OH)_p$ where $p$ is a number from three to about eight; and Z is selected from the group consisting of bivalent alkylene radicals carrying at least one HS group in a position alpha or beta to a COOR group, and such radicals containing at least one additional group selected from carboxylic acid, carboxylic ester, and mercapto groups; the ester and the α-olefin being in a molar ratio ester: α-olefin within the range from 1:1 to 1:8; the α-olefin and the ester being reacted in the presence of a free radical catalyst providing a free radical in the reaction mixture of a temperature at which the reaction proceeds up to about 200° C, and recovering the resulting reaction mixture substantially without purification as a stabilizer mixture for poly-α-olefins.

13. A process according to claim 12, in which the mercaptocarboxylic acid is 3-mercaptopropionic acid.

14. A process according to claim 12, in which the polyhydric alcohol is pentaerythritol.

15. A process according to claim 12, in which the polyhydric acid is tris (hydroxyethyl) isocyanurate.

16. A process according to claim 12, in which the polyhydric alcohol is tris (methylol) propane.

17. A process according to claim 12, in which the α-olefin is hexadecene.

18. A process according to claim 12, in which the α-olefin is octadecene.

19. A process according to claim 12, in which the α-olefin is eicosene.

20. A process according to claim 12, in which the reaction temperature is within the range from about 50° to about 120° C.

21. A process according to claim 12, in which the catalyst is an organic peroxide.

22. A process according to claim 12, in which the catalyst is an azo compound.

23. A poly-α-olefin resin composition having an enhanced resistane to deterioration in physical properties when exposed to light, air, and heat, comprising a poly-α-olefin resin and a stabilizing concentration of a stabilizer mixture according to claim 1.

24. A poly-α-olefin resin composition according to claim 23, in which the mercaptocarboxylic acid is 3-mercaptopropionic acid.

25. A poly-α-olefin resin composition according to claim 23, in which the polyhydric alcohol is pentaerythritol.

26. A poly-α-olefin resin composition according to claim 23, in which the polyhydric alcohol is tris (hydroxyethyl) isocyanurate.

27. A poly-α-olefin resin composition according to claim 23, in which the polyhydric alcohol is tris (methylol) propane.

28. A poly-α-olefin resin composition according to claim 23, in which the α-olefin is hexadecene.

29. A poly-α-olefin resin composition according to claim 23, in which the α-olefin is octadecene.

30. A poly-α-olefin resin composition according to claim 23, in which the α-olefin is eicosene.

31. A poly-α-olefin resin composition according to claim 23, in which the mercaptocarboxylic acid is in combination with an antioxidant.

32. A poly-α-olefin resin composition according to claim 23, in which the antioxidant is a phenol.

33. A poly-α-olefin resin composition according to claim 31, in which the antioxidant is an organic phosphite.

* * * * *

UNITED STATES PATENT OFFICE
CERTIFICATE OF CORRECTION

Patent No. 4,080,364　　　　　　　　Dated March 21, 1978

Inventor(s)　Otto S. Kauder et al

It is certified that error appears in the above-identified patent and that said Letters Patent are hereby corrected as shown below:

Column 1, lines 50 and 51, formula should all be on one line,
-- $-XO[OCCH_2CH_2SCH_2CH_2COOXO]_n OCCH_2CH_2-S-CH_2CH_2COOZ$ --

Column 2, line 57, "$(CH_2CH_2CH)CH_3)SCH_2CH_2COOH)$" should be
-- $(CH_2CH_2CH(CH_3)SCH_2CH_2COOH)$ --

Column 3, line 39, "didecylthiopro-" should be --dodecylthiopro- --

Column 6, line 57, "diperoxy2" should be --diperoxy-2-- line 63, "yclohexane" should be --cyclohexane-- line 66, "peoxides" should be --peroxides--

Column 7, lines 12 to 13, delete "tertiary-butylperoxy isopropyl carbonates, such as"

line 23, "2, 5-dimethylhexane2, 5-dihydroperoxide" should be --2, 5-dimethylhexane-2, 5-dihydroperoxide-- line 27, "a, a:bis" should be --$\alpha, \alpha'$:bis-- line 28, "(tertiary-butyl peroxydiisopropylbenzene" should be --(tertiary-butyl peroxy) diisopropylbenzene--

UNITED STATES PATENT OFFICE
CERTIFICATE OF CORRECTION

Patent No. 4,080,364    Dated March 21, 1978

Inventor(s) Otto S. Kauder et al

It is certified that error appears in the above-identified patent and that said Letters Patent are hereby corrected as shown below:

Column 8, line 57, " 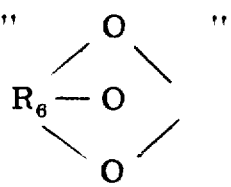 " should be 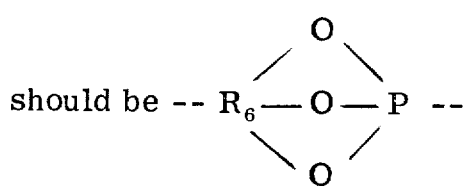

Column 9, line 3, "phosphite" should be --phosphites-- line 33, insert --Z-- before "is"

line 36, insert --Z-- before "can"

Column 10, line 5, "pentaerythrityl" should be --pentaerythritol-- line 8, "di(decycloxy)" should be --di(decyloxy)-- line 12, "3phenoxy" should be --3-phenoxy-- lines 29 & 30, "(methoxyethoxethyloxy)" should be --(methoxyethoxyethoxyethyloxy)-- line 54, "4,4'n" should be --4,4'-n-- line 56, "butyl5" should be --butyl-5-- line 60, "tetra-tridecyl4,4' " should be --tetra-tridecyl-4,4'--

Column 11, line 12, "compond" should be --compound--

UNITED STATES PATENT OFFICE
CERTIFICATE OF CORRECTION

Patent No. 4,080,364   Dated March 21, 1978

Inventor(s) Otto S. Kauder et al

It is certified that error appears in the above-identified patent and that said Letters Patent are hereby corrected as shown below:

| | | |
|---|---|---|
| Column 15, line 14 | : | "2,6diisopro" should be --2,6-diisopro-- |
| Column 16, line 15 | : | "5-methylbenzoyln" should be -- 5-methylbenzoyl-n- -- |
| Column 17, line 35 | : | " (c) $R_1O[OCCH_2CH_2SCH_2CH_2COOX\text{-}O]_nOCCH_2CH_2SCH_2CH_2COOZ$ " should be -- (c) $R_1O[OCCH_2CH_2SCH_2CH_2COOX\text{-}O]_nOCCH_2CH_2SCH_2CH_2COOZ$ -- |
| Column 19, line 28 | : | "oxy encontaining" should be -- oxygen containing -- |
| Column 20, line 37 | : | Delete "b" before "0.0001" |
| Column 21, line 34 | : | "or" should be --on-- |
| Column 22, line 66 | : | "found" should be --round-- |
| Column 23, line 11 | : | "from" should be --found-- |
| line 27 | : | Insert --carbon-- before "atoms" |
| Column 24, line 14 | : | "found" should be --round-- |
| line 52 | : | "found" should be --round-- |
| Column 26, line 52 | : | "XVII" should be --XVIII-- |
| Column 29, line 12 | : | "twophase" should be --two-phase-- |

UNITED STATES PATENT OFFICE
CERTIFICATE OF CORRECTION

Patent No. 4,080,364                Dated March 21, 1978

Inventor(s) Otto S. Kauder et al

It is certified that error appears in the above-identified patent and that said Letters Patent are hereby corrected as shown below:

Column 37, add --Waxy deposit at two hours-- opposite Example 25 under heading "190°C oven test".

Column 40, claim 32, line 35, "23" should be --31--.

Signed and Sealed this

Third Day of October 1978

[SEAL]

Attest:

RUTH C. MASON
Attesting Officer

DONALD W. BANNER
Commissioner of Patents and Trademarks